(12) United States Patent
Kelly et al.

(10) Patent No.: US 9,707,330 B2
(45) Date of Patent: Jul. 18, 2017

(54) DUAL FLOW SORBENT CARTRIDGE

(75) Inventors: Thomas D. Kelly, Highland Park, IL (US); SuPing Lyu, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 571 days.

(21) Appl. No.: 14/240,129

(22) PCT Filed: Aug. 22, 2012

(86) PCT No.: PCT/US2012/051946
§ 371 (c)(1),
(2), (4) Date: Jul. 14, 2014

(87) PCT Pub. No.: WO2013/028809
PCT Pub. Date: Feb. 28, 2013

(65) Prior Publication Data
US 2014/0326671 A1    Nov. 6, 2014

Related U.S. Application Data

(60) Provisional application No. 61/526,209, filed on Aug. 22, 2011.

(51) Int. Cl.
*A61M 1/16* (2006.01)
*A61M 1/36* (2006.01)
(Continued)

(52) U.S. Cl.
CPC ............ *A61M 1/1696* (2013.01); *A61M 1/16* (2013.01); *A61M 1/3609* (2014.02); *B01D 15/00* (2013.01);
(Continued)

(58) Field of Classification Search
CPC .... A61M 1/16; A61M 1/1696; A61M 1/3609; A61M 2205/75; A61M 2205/3313;
(Continued)

(56) References Cited

U.S. PATENT DOCUMENTS 3,608,729 A    9/1971   Haselden
3,669,880 A    6/1972   Marantz
(Continued)

FOREIGN PATENT DOCUMENTS

EP    1592494 B1    6/2009
EP    1345856 B1    3/2013
(Continued)

OTHER PUBLICATIONS

Search Report of corresponding European Patent Application No. 12826180 issued on Mar. 11, 2015.*
(Continued)

*Primary Examiner* — John Kim
(74) *Attorney, Agent, or Firm* — Kenneth Collier; Roger Hahn

(57) ABSTRACT

Disclosed are systems and methods for the performance of kidney replacement therapy having or using a dialyzer, control components, a sorbent cartridge with at least two separate flow paths, and fluid reservoirs configured to be of a weight and size suitable to be worn or carried by an individual requiring treatment. The system for performing kidney replacement therapy has a controlled compliance dialysis circuit, where a control pump controls the bi-directional movement of fluid across a dialysis membrane. The dialysis circuit and an extracorporeal circuit for circulating blood are in fluid communication through the dialysis membrane. The flux of fluid moving between the extracorporeal circuit and the dialysis circuit is modified by the rate at which the control pump is operating such that a rate of (Continued)

ultrafiltration and convective clearance can be controlled. The system provides for the monitoring of an inlet and outlet conductivity of the sorbent cartridge to provide a facility to quantify or monitor the removal of urea by the sorbent cartridge.

24 Claims, 14 Drawing Sheets

(51) Int. Cl.
  *B01J 20/20* (2006.01)
  *B01J 20/02* (2006.01)
  *B01J 20/24* (2006.01)
  *B01D 15/00* (2006.01)
  *B01D 15/02* (2006.01)

(52) U.S. Cl.
  CPC ............ *B01D 15/02* (2013.01); *B01J 20/0211* (2013.01); *B01J 20/0292* (2013.01); *B01J 20/20* (2013.01); *B01J 20/24* (2013.01); *A61M 2205/3313* (2013.01); *A61M 2205/3317* (2013.01); *A61M 2205/75* (2013.01); *A61M 2209/082* (2013.01); *B01D 2313/44* (2013.01); *B01J 2220/62* (2013.01)

(58) Field of Classification Search
  CPC .... A61M 2205/3317; A61M 2209/082; B01D 15/00; B01D 15/22; B01D 2313/44; B01J 20/0211; B01J 20/0292; B01J 20/20; B01J 20/24; B01J 2220/62
  See application file for complete search history.

(56) References Cited

U.S. PATENT DOCUMENTS

| | | | |
|---|---|---|---|
| 3,776,819 A | 12/1973 | Williams | |
| 3,850,835 A | 11/1974 | Marantz | |
| 3,884,808 A | 5/1975 | Scott | |
| 3,902,490 A | 9/1975 | Jacobsen et al. | |
| 3,989,622 A | 11/1976 | Marantz | |
| 4,094,775 A | 6/1978 | Mueller | |
| 4,206,054 A * | 6/1980 | Moore ............... | A01K 63/045 210/167.23 |
| 4,209,392 A | 6/1980 | Wallace | |
| 4,376,707 A | 3/1983 | Lehmann | |
| 4,460,555 A | 7/1984 | Thompson | |
| 4,581,141 A | 4/1986 | Ash | |
| 4,650,587 A | 3/1987 | Polak | |
| 4,684,460 A * | 8/1987 | Issautier ............ | A61M 1/1696 210/143 |
| 5,230,702 A | 7/1993 | Lindsay et al. | |
| 5,284,470 A | 2/1994 | Beltz | |
| 5,302,288 A | 4/1994 | Meidl | |
| 5,308,315 A | 5/1994 | Khuri | |
| 5,507,723 A | 4/1996 | Keshaviah | |
| 5,662,806 A | 9/1997 | Keshaviah et al. | |
| 5,849,179 A | 12/1998 | Emerson et al. | |
| 5,858,186 A | 1/1999 | Glass | |
| 5,944,684 A | 8/1999 | Roberts | |
| 6,036,858 A * | 3/2000 | Carlsson ............ | A61M 1/1656 210/232 |
| 6,114,176 A | 9/2000 | Edgson et al. | |
| 6,126,831 A | 10/2000 | Goldau et al. | |
| 6,521,184 B1 | 2/2003 | Edgson et al. | |
| 6,627,164 B1 | 9/2003 | Wong | |
| 6,666,840 B1 | 12/2003 | Falkvall et al. | |
| 6,719,745 B1 | 4/2004 | Taylor | |
| 6,814,724 B2 | 11/2004 | Taylor | |
| 6,818,196 B2 | 11/2004 | Wong | |
| 6,861,266 B1 | 3/2005 | Sternby | |
| 6,878,283 B2 | 4/2005 | Thompson | |
| 6,960,179 B2 | 11/2005 | Gura | |
| 7,033,498 B2 | 4/2006 | Wong | |
| 7,101,519 B2 | 9/2006 | Wong | |
| 7,208,092 B2 | 4/2007 | Micheli | |
| 7,241,272 B2 | 7/2007 | Karoor | |
| 7,276,042 B2 | 10/2007 | Polaschegg et al. | |
| 7,326,576 B2 | 2/2008 | Womble et al. | |
| 7,435,342 B2 | 10/2008 | Tsukamoto | |
| 7,488,447 B2 | 2/2009 | Sternby | |
| 7,537,688 B2 | 5/2009 | Tarumi et al. | |
| 7,544,300 B2 | 6/2009 | Brugger et al. | |
| 7,544,737 B2 | 6/2009 | Poss et al. | |
| 7,563,240 B2 | 7/2009 | Gross et al. | |
| 7,566,432 B2 | 7/2009 | Wong | |
| 7,597,806 B2 | 10/2009 | Uchi et al. | |
| 7,776,210 B2 | 8/2010 | Rosenbaum | |
| 7,794,419 B2 | 9/2010 | Paolini et al. | |
| 7,850,635 B2 | 12/2010 | Polaschegg et al. | |
| 7,922,686 B2 | 4/2011 | Childers et al. | |
| 7,922,911 B2 | 4/2011 | Micheli | |
| 7,947,179 B2 | 5/2011 | Rosenbaum | |
| 7,955,290 B2 | 6/2011 | Karoor et al. | |
| 7,988,854 B2 | 8/2011 | Tsukamoto | |
| 8,002,726 B2 | 8/2011 | Karoor | |
| 8,012,118 B2 | 9/2011 | Curtin | |
| 8,029,454 B2 | 10/2011 | Kelly et al. | |
| 8,066,658 B2 | 11/2011 | Karoor et al. | |
| 8,080,161 B2 | 12/2011 | Ding et al. | |
| 8,087,303 B2 | 1/2012 | Beavis | |
| 8,096,969 B2 | 1/2012 | Roberts | |
| 8,180,574 B2 | 5/2012 | Lo et al. | |
| 8,187,250 B2 | 5/2012 | Roberts | |
| 8,197,439 B2 | 6/2012 | Wang et al. | |
| 8,303,532 B2 | 11/2012 | Hamada et al. | |
| 8,404,091 B2 | 3/2013 | Ding et al. | |
| 8,409,444 B2 | 4/2013 | Wong | |
| 8,480,607 B2 | 7/2013 | Davies | |
| 8,647,506 B2 | 2/2014 | Wong | |
| 8,733,559 B2 | 5/2014 | Wong | |
| 8,764,981 B2 | 7/2014 | Ding | |
| 8,777,892 B2 | 7/2014 | Sandford | |
| 9,144,640 B2 | 9/2015 | Pudil | |
| 2002/0112609 A1 | 8/2002 | Wong | |
| 2003/0080059 A1 | 5/2003 | Peterson et al. | |
| 2003/0097086 A1 | 5/2003 | Gura | |
| 2003/0105435 A1 | 6/2003 | Taylor | |
| 2003/0114787 A1 | 6/2003 | Gura | |
| 2004/0019312 A1 | 1/2004 | Childers et al. | |
| 2004/0099593 A1 | 5/2004 | DePaolis | |
| 2004/0147900 A1 | 7/2004 | Polaschegg | |
| 2005/0006296 A1 | 1/2005 | Sullivan | |
| 2005/0113796 A1 | 5/2005 | Taylor | |
| 2005/0150832 A1 | 7/2005 | Tsukamoto | |
| 2005/0274658 A1 | 12/2005 | Rosenbaum | |
| 2006/0241543 A1 | 10/2006 | Gura | |
| 2007/0007208 A1 | 1/2007 | Brugger et al. | |
| 2007/0179431 A1 | 8/2007 | Roberts | |
| 2007/0213665 A1 | 9/2007 | Curtin | |
| 2008/0006570 A1 | 1/2008 | Gura | |
| 2008/0051696 A1 | 2/2008 | Curtin | |
| 2008/0053905 A9 | 3/2008 | Brugger et al. | |
| 2009/0020471 A1 | 1/2009 | Tsukamoto | |
| 2009/0078636 A1 | 3/2009 | Uchi | |
| 2009/0101552 A1 | 4/2009 | Fulkerson | |
| 2009/0120864 A1 | 5/2009 | Fulkerson | |
| 2009/0157877 A1 | 6/2009 | Baek | |
| 2009/0216045 A1 | 8/2009 | Singh | |
| 2010/0004588 A1 | 1/2010 | Yeh et al. | |
| 2010/0007838 A1 | 1/2010 | Fujimoto | |
| 2010/0078381 A1 | 4/2010 | Merchant | |
| 2010/0084330 A1 | 4/2010 | Wong | |
| 2010/0100027 A1 | 4/2010 | Schilthuizen et al. | |
| 2010/0102190 A1 | 4/2010 | Zhu et al. | |
| 2010/0114012 A1 | 5/2010 | Sandford et al. | |
| 2010/0217181 A1 | 8/2010 | Roberts | |
| 2010/0224492 A1 | 9/2010 | Ding et al. | |
| 2010/0314314 A1 | 12/2010 | Ding | |
| 2011/0009798 A1 | 1/2011 | Kelly | |
| 2011/0017665 A1 | 1/2011 | Updyke | |
| 2011/0048949 A1 | 3/2011 | Ding | |

(56) References Cited

U.S. PATENT DOCUMENTS

| | | |
|---|---|---|
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2012/0018377 A1 | 1/2012 | Tsukamoto |
| 2012/0248017 A1 | 10/2012 | Beiriger |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0190885 A1 | 7/2014 | Meyer |
| 2014/0217028 A1 | 8/2014 | Pudil |
| 2014/0251908 A1 | 9/2014 | Ding |
| 2014/0326671 A1 | 11/2014 | Kelly |
| 2015/0057602 A1 | 2/2015 | Mason |
| 2015/0108609 A1 | 4/2015 | Kushida |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |

FOREIGN PATENT DOCUMENTS

| | | |
|---|---|---|
| EP | 2344220 B1 | 4/2013 |
| WO | 9532010 A1 | 11/1995 |
| WO | 0185295 A2 | 11/2001 |
| WO | 0243859 | 6/2002 |
| WO | 03043677 A2 | 5/2003 |
| WO | 03051422 A2 | 6/2003 |
| WO | 2004064616 A2 | 8/2004 |
| WO | 2005123230 A2 | 12/2005 |
| WO | 2007089855 A2 | 8/2007 |
| WO | 2008075951 | 6/2008 |
| WO | 2010028860 A1 | 2/2010 |
| WO | 2013019179 | 2/2013 |
| WO | 2013025957 | 2/2013 |
| WO | 2013027214 | 2/2013 |
| WO | 2013028809 | 2/2013 |
| WO | 2013019994 A3 | 4/2013 |
| WO | 2012060700 | 5/2013 |
| WO | 2013025844 A3 | 5/2013 |
| WO | 2013103607 A1 | 7/2013 |
| WO | 2013103906 | 7/2013 |
| WO | 2015142624 | 9/2015 |
| WO | 2015199764 | 12/2015 |

OTHER PUBLICATIONS

U.S. Appl. No. 61/526,209, filed Aug. 22, 2011.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
PCT/US2014/065950 International Search Report and Written Opinion mailed Feb. 24, 2015.
PCT/US2015/032492 International Search Report mailed Nov. 19, 2015.
PCT/US2015/016270 International Search Report and Written Opinion mailed Jun. 5, 2015.
PCT/US2015/016273 International Search Report and Written Opinion mailed Jun. 9, 2015.
PCT/US2015/032492 Written Opinion mailed Nov. 19, 2015.
PCT/US2015/020046 International Search Report and Written Opinion mailed Jun. 29, 2015.
PCT/US2015/020044 International Search Report Written Opinion mailed Jun. 30, 2015.
PCT/US15/18587 International Preliminary Report on Patentability Dated Jun. 6, 2016.
European Search Opinion for App. No. EP12826180 Dated Mar. 19, 2015.
European Search Opinion for App. No. EP12826180 Dated Jan. 18, 2016.

* cited by examiner

DUAL FLOW SORBENT CARTRIDGE

CROSS-REFERENCE TO RELATED APPLICATIONS

This application claims the benefit of priority to International Application Serial No. PCT/US2012/051946, filed on Aug. 22, 2012, and to U.S. Provisional Application Ser. No. 61/526,209, filed on Aug. 22, 2011, both of which are incorporated herein by reference.

FIELD OF THE INVENTION

The invention relates to sorbent cartridges for regeneration of dialysate in hemodialysis systems, including portable and systems, for hemodialysis and hemofiltration for the treatment of pathological conditions such as End Stage Renal Disease (ESRD). The systems and methods include a system having a dialyzer, control components, and a sorbent cartridge for dialysate configured to conserve zirconium-based materials and increase system safety. Further, the systems and methods include a sorbent cartridge having two flow paths through the sorbent cartridge for dialysate regeneration. The disclosure further relates to the treatment of Chronic Kidney Disease (CKD) through methods and apparatuses that allow an individual to remain ambulatory during treatment.

BACKGROUND

Dialysis is the most commonly applied physical principle to address the build-up of urea in the blood of patients with kidney failure. Dialysis membranes employed in dialysis treatment are typically only selective toward molecular weight and not toward other properties such as charge. As such, urea, ions and other small molecules can move across the dialysis membrane unimpeded from a higher concentration to a lower concentration, thereby lowering the concentration of such species in the patient's blood. Waste species entering the dialysate and impurities are removed by a sorbent cartridge before the dialysate is reused for dialysis.

In order for spent dialysate to be reused, accumulated waste products and impurities must be removed from the spent dialysate, and the composition and pH of the regenerated dialysate must be regulated for physiological compatibility. Devices that regenerate spent dialysis fluid for reuse are primarily directed toward the removal of urea, ammonium ions, uric acid, creatinine, and phosphate via various sorbents. For example, the Recirculating Dialysate System ("REDY system"), which was introduced in the 1970s, employs a sorbent cartridge through which spent dialysate is recirculated and regenerated. However, the regenerated dialysate produced by REDY systems is subject to variations in pH and sodium requiring ongoing adjustment.

Moreover, traditional dialysis systems employing sorbent technology, such as the REDY system usually employ low-flux dialyzers and adjust dialysate pressure to achieve net patient fluid removal. The UF coefficient of a dialyzer specifies the rate of filtration through the dialyzer due to pressure differences across the dialyzer membrane, typically called the trans-membrane pressure. The trans-membrane pressure is calculated by the formula TMP=((Blood Inlet Pressure+Blood Outlet Pressure)/2)−((Dialysate Inlet Pressure+Dialysate Outlet Pressure)/2). This formula is usually shortened to TMP=Venous Return Pressure−Dialysate Pressure. Low flux hemodialyzers have a UF coefficient of less than 8 ml of water flux per hour per mmHg of trans-membrane pressure. To illustrate fluid removal with the traditional sorbent system, a typical low flux dialyzer could have a UF coefficient of 4 mL/hr/mmHg. To calculate the pressure necessary to achieve the rate of fluid removal, the desired hourly fluid removal is divided by the dialyzer UF coefficient. For example, an hourly rate of 0.5 L/hr yields a required trans-membrane pressure (TMP) of 125 mmHg if the UF coefficient is 4 mL/hr/ mmHg. 125 mmHg is the trans-membrane pressure required to remove fluid at a rate of 0.5 L per hour. The venous pressure is a function of the blood flow rate and the blood return restriction (needle and access). As the Venous Return Pressure cannot be set, to control the fluid removal rate it is necessary calculate the required dialysate pressure. The operator calculates dialysate pressure via the formula Dialysate Pressure=Venous Pressure−TMP, if the venous return pressure were 75 mmHg, (DP=75−125=−50 mmHg). In this example the user must adjust the dialysate pressure to −50 mmHg to achieve the TMP of 125 mmHg. The venous pressure fluctuates during treatment so the operator must adjust the dialysate pressure on a regular basis, which is not suitable for a non-medical professional or a home patient. With high-flux dialyzers, pressure alone is not accurate enough to control ultrafiltration because fluid moves more freely across the dialyzer membrane. To control ultrafiltration in conventional hemodialysis using high-flux dialyzers, balancing chambers, flow sensors or other methods to balance flow to and from the dialyzer are employed. In CRRT (continuous blood purification machine) equipment, pumps controlled by precise scales are required to control the flow to and from the dialyzer very accurately.

Further development of dialysate recirculating techniques has resulted in systems that employ a variety of sorbent media, including activated carbon, urease, and zirconium-, aluminum-, and magnesium-based compounds. One of the problems associated with sorbent regeneration of spent dialysate is the buildup of sodium ions released as a byproduct of the absorption process, which operates by cation exchange. Further, electrolytes such as calcium, magnesium, and potassium are removed from spent dialysate by sorbent and deionization media and must be added back to the dialysate prior to reuse, which degrades the useful lifetime of cation exchange materials used as sorbent media.

Moreover, the sorbent cartridge is usually formed of expensive materials such as zirconium-based materials. Urea, the main metabolic waste product found in the blood, is a neutral, water-miscible compound making urea difficult to remove from the dialysate through absorption of large quantities. Urea is converted by an enzyme present in the sorbent cartridge to convert urea to ammonia and carbon dioxide. At the slightly basic pH of the dialysate, ammonia is present as positively-charged ammonium ions that are more easily absorbed by ion exchange materials. However, the use of ion exchange materials to remove urea/ammonium also removes other electrolytes that are present in the dialysate to maintain physiological compatibility, including $Mg^{2+}$, $Ca^{2+}$ and $K^+$. A large portion of the cation absorption capacity, and hence ammonium absorption capability, provided by the zirconium materials of the sorbent cartridge is consumed by the absorption of $Mg^{2+}$, $Ca^{2+}$ and $K^+$. There is a clear need for preserving ammonium absorption capability.

U.S. Pat. No. 3,669,878 Marantz et al. describes sorbent removal of urea and ammonium ions from spent dialysate via urease, ammonium carbonate, and zirconium phosphate, U.S. Pat. No. 3,669,880 Marantz et al. describes directing a controlled volume of dialysate through zirconium phosphate, activated carbon, and hydrated zirconium oxide columns, U.S. Pat. No. 3,850,835 Marantz et al. describes production of a zirconium hydrous oxide ion exchange media, and U.S. Pat. No. 3,989,622 Marantz et al. describes absorption of urease on aluminum oxide and magnesium silicate media to convert liquid urea to ammonium carbonate. U.S. Pat. No. 4,581,141 Ash describes removal of uremic waste species from dialysate via a calcium-based cation exchanger, urease, and aliphatic carboxylic acid resin. U.S. Pat. No. 4,826,663 Alberti et al. describes a method of preparing a zirconium phosphate ion exchanger. U.S. Pat. No. 6,627,164 Wong describes production of sodium zirconium carbonate for ion exchange in renal dialysis, and U.S. Pat. No. 7,566,432 Wong describes production of zirconium phosphate particles for ion exchange in regenerative dialysis. U.S. Pat. No. 6,818,196 Wong, U.S. Pat. No. 7,736,507 Wong, U.S. Application Publication 2002/0112609 Wong, U.S. Application Publication 2010/0078387 Wong, and U.S. Application Publication 2010/00784330 Wong, describe cartridges for purification of dialysis solutions using sodium zirconium carbonate. U.S. Pat. No. 6,878,283 Thompson, U.S. Pat. No. 7,776,210 Rosenbaum et al., U.S. Application Publication 2010/0326911 Rosenbaum et al., U.S. Application Publication 2010/0078381 Merchant, U.S. Application Publication 2009/0127193 Updyke et al. and U.S. Application Publication 2011/0017665 Updyke et al. describe filter cartridges having a plurality of types of filter media including zirconium compounds, urease, and alumina for dialysis systems. WO 2009/157877 A1 describes a urease material having urease immobilized on a substrate intermixed with a cation exchange material or zirconium phosphate material to improve workability for the reduction of clogging and to improve absorption of ammonium ions generated by the urease.

With regard to the management of impurities in regenerated dialysate, U.S. Pat. No. 4,460,555 Thompson and U.S. Pat. No. 4,650,587 Polak et al. describes magnesium phosphate media for removal of ammonia from aqueous solutions. U.S. Application Publication 2009/0282980 Gura et al. describes degassing devices for use in dialysate systems having urease media.

There is a need for unsupervised operation in mobile or home-based systems by a patient that maximizes the safety of the system to levels beyond those required for operation in a clinical setting. There is also a need to reduce the cost of consumable materials, such as the sorbent cartridge, that are covered by a single patient utilizing a mobile or at home-based system. Further, there remains a need for patient-friendly wearable and/or portable dialysis systems (collectively also referred to as mobile-based systems) that are capable of operating on a small volume of dialysate and suitable for daily continuous or short-term dialysis.

SUMMARY OF THE INVENTION

The invention is directed to a dialysis system having a size and weight suitable to be carried or worn by a patient during a dialysis treatment. In any embodiment, a sorbent cartridge has at least one cartridge body having a first inlet port and a second inlet port, which are both in fluid communication with an outlet port, wherein the first inlet port defines a first flow path and the second inlet port defines a second flow path. The first flow path has at least one interior space or sorbent material in the cartridge body that is not in fluid communication with the second flow path. Further, the sorbent cartridge is capable of removing at least one impurity or waste species from a fluid. The sorbent cartridge has two flow paths for regenerating a dialysate.

In any embodiment, a first flow path of a sorbent cartridge can pass a fluid though any one of a urease-containing material, a zirconium phosphate material, a zirconium oxide material and an activated carbon material and combinations thereof.

In any embodiment, a second flow path of a sorbent cartridge can pass a fluid through any one of a mixed anion and cation de-ionization resin and an activated carbon material and combinations thereof.

In any embodiment, a fluid introduced to a first inlet port of a sorbent cartridge passes through a third interior space but does not pass through a fourth interior space.

In any embodiment, a fluid introduced to a second inlet port of a sorbent cartridge passes through a fourth interior space but does not pass through a third interior space.

In any embodiment, a fluid introduced to a second inlet port of a sorbent cartridge passes through a fourth interior space but does not pass through a third interior space and a second interior space.

In any embodiment, a fluid introduced to a second inlet port of a sorbent cartridge passes through a fourth interior space but does not pass through the a interior space and a first interior space.

In any embodiment, the sorbent cartridge of the invention can be used in a portable dialysis system, which has a dialyzer having a dialysis membrane, a blood inlet end for receiving blood, a blood outlet end for allowing blood out of the dialyzer, a dialysate inlet end for receiving dialysate and a dialysate outlet end for allowing dialysate out of the dialyzer, wherein the blood and the dialysate contact different sides of the dialysis membrane. Blood is circulated through the dialyzer with an extracorporeal circuit having a conduit for receiving blood from a subject and a conduit for returning blood to a subject, a blood pump for conveying blood from the subject through the extracorporeal circuit and the dialyzer, wherein blood is conveyed from the subject, to the dialyzer and back to the subject. Dialysate is conveyed through the dialyzer with a dialysis circuit having a sorbent cartridge for removing impurities and wastes species from the dialysate, one or more conduits for carrying dialysate between the sorbent cartridge and the dialyzer, and a dialysate pump for conveying dialysate from the sorbent cartridge, to the dialyzer and back to the sorbent cartridge, the sorbent cartridge having a dialysate inlet end and a dialysate outlet end.

In any embodiment, a first flow path includes a urease material and a zirconium phosphate material. The first flow path includes any one of a urease-containing material, a zirconium phosphate material, a zirconium oxide material and an activated carbon material and combinations thereof and a second flow path includes any one of a mixed anion and cation de-ionization resin and an activated carbon material and combinations thereof. The sorbent cartridge includes first and second cartridge bodies, wherein the first input port allows a fluid to enter one cartridge body and the second inlet port allows a fluid to enter the second cartridge body.

In any embodiment, a second cartridge body has an outlet port attached to a conduit for passing fluid to a side port of another cartridge body. The sorbent cartridge has one cartridge body having a top portion and top portion sidewall and a bottom portion and bottom portion sidewall, the bottom portion having a larger mean diameter than the top portion, wherein a downstream opening and an upstream opening of the cartridge body are substantially parallel. A first molded housing has a first interior space formed from one or more sidewalls and the one or more sidewalls forming a downstream opening and an upstream opening to the first molded housing, and having a plurality of standoffs projecting from the first molded housing in a direction perpendicular to the downstream opening. A second molded housing has a third interior space formed from one or more sidewalls and the one or more sidewalls forming a downstream opening and an upstream opening to the second molded housing, the second molded housing having an annular peripheral portion having a plurality of openings formed therein downstream. The first molded housing is located interior to the cartridge body, where the downstream opening and upstream opening of the first molded housing are parallel to the downstream opening and upstream opening of the cartridge body, and a first interior space is formed between the downstream opening of the first molded housing and the downstream opening of the cartridge body, and a first flow channel space is formed between the one or more sidewalls of the first molded housing and the sidewall of the cartridge body. The second molded housing is located interior to the cartridge body, where the downstream opening and upstream opening of the second molded housing are parallel to the downstream opening and upstream opening of the cartridge body, and a fourth interior space is formed between the one or more sidewalls of the second molded housing and the one or more sidewalls of the cartridge body, wherein the fourth interior space is in fluid communication with the first flow channel space.

In any embodiment, a sorbent cartridge has a cartridge body having a top portion and top portion sidewall and a bottom portion and bottom portion sidewall, the bottom portion having a larger mean diameter than the top portion, wherein a downstream opening and an upstream opening of the cartridge body are substantially parallel.

In any embodiment, a sorbent cartridge has one or more molded housings present within the cartridge body, wherein a first interior space is formed between a downstream opening of one of the molded housing and the downstream opening of the cartridge body with the proviso that the first interior space is not interior to the one or more molded housings.

In any embodiment, one or more molded housings include a first molded housing having a second interior space formed from one or more sidewalls and the one or more sidewalls forming a downstream opening and an upstream opening to the first molded housing.

In any embodiment, one or more molded housings include a second molded housing having a third interior space formed from one or more sidewalls and the one or more sidewalls forming a downstream opening and an upstream opening to the second molded housing.

In any embodiment, a second molded housing has an annular peripheral portion having a plurality of openings formed therein.

In any embodiment, a first molded housing has a plurality of standoffs projecting from the first molded housing in a direction substantially perpendicular to the downstream opening of the cartridge body.

In any embodiment, a first flow channel space is formed between the one or more sidewalls of the first molded housing and the sidewall of a cartridge body.

In any embodiment, a downstream opening and an upstream opening of a second molded housing are parallel to a downstream opening and an upstream opening of a cartridge body, and a fourth interior space is formed between the one or more sidewalls of the second molded housing and the one or more sidewalls of the cartridge body.

In any embodiment, one or more molded housings include a first molded housing having a second interior space formed from one or more sidewalls and the one or more sidewalls forming a downstream opening and an upstream opening to the first molded housing, and the one or more molded housings include a second molded housing having a third interior space formed from one or more sidewalls and the one or more sidewalls forming a downstream opening and an upstream opening to the second molded housing.

In any embodiment, a sorbent cartridge has a first flow channel space formed between one or more sidewalls of a first molded housing and the sidewall of the cartridge body.

In any embodiment, a sorbent cartridge has a fourth interior space that is in fluid communication with a first flow channel space.

In any embodiment, a first flow path and a second flow path are entirely contained within the one cartridge body.

In any embodiment, a second molded housing has an annular peripheral portion that contacts one or more sidewalls of a cartridge body.

In any embodiment, a sorbent cartridge has a first molded housing that contacts a second molded housing.

In any embodiment, a control pump controls the bi-directional movement of fluid into and out of the dialysis circuit, where a flux of fluid moving between the extracorporeal circuit and the dialysis circuit is changed by the rate at which the control pump is operating, and a control reservoir stores fluid removed from the dialysis circuit by the control pump or stores fluid that can be added to the dialysis circuit by the control pump.

In any embodiment, a second reservoir and a second reservoir pump is present to add water to the dialysis circuit, where fluid added to the dialysis circuit causes movement of fluid from the dialysis circuit to the extracorporeal circuit.

In any embodiment, the dialysis system has an infusate reservoir containing an infusate containing one or more electrolytes selected from potassium ions, calcium ions, and magnesium ions. The infusate is added to the dialysate under the control of a controller in order to maintain the concentration of potassium ion, calcium ion and/or magnesium ion within predetermined ranges.

In any embodiment, the dialysate is conveyed through the dialysis system by a dialysate pump, where the rate of the dialysate pump is controlled by a controller. Blood from a patient is conveyed through the dialysis system by a blood pump, wherein the blood pump is controlled by a controller. One or more impurities from a fluid and the sodium ion concentration are adjusted by measuring the conductivity of the fluid prior to entering a sorbent cartridge, dividing the fluid between a first inlet port and a second inlet port of the sorbent cartridge based upon the conductivity of the fluid; and recovering the fluid from an outlet port of the sorbent cartridge. The sorbent cartridge has a first flow path connected to the first inlet port including a urease material and a second flow path connected to the second inlet port including a mixed bed anion and cation exchange material.

In any embodiment, a blood hydration status monitor monitors the relative blood hydration status of the subject's blood in the extracorporeal circuit. A hematocrit detector monitors the hematocrit of the subject's blood in the extracorporeal circuit. In certain embodiments, pulsatile pumps are not used to convey the blood or the dialysate. Enhanced convective clearance is performed utilizing the controlled compliance dialysis circuit by operating the control pump in a bidirectional manner with intermittent reversal of the direction of operation.

In any embodiment, a method is implemented using a sorbent cartridge for removal of a waste species including attaching the vasculature of a subject to a system for kidney replacement therapy, the system having an extracorporeal circuit having a first end that draws blood from the subject and a second end that returns blood to the subject, and a controlled compliance dialysis circuit, where the extracorporeal circuit and the dialysis circuit in fluid communication through a dialysis membrane housed in a dialyzer. Blood is conveyed from the subject through the extracorporeal circuit and the dialyzer and returned to the subject. A dialysate is conveyed through the dialysis circuit such that the dialysate moves from the sorbent cartridge, to the dialyzer and back to the sorbent cartridge, where at least one waste species diffuses from the blood to the dialysate through the dialysis membrane and the sorbent cartridge substantially removes at least one impurity or waste species from the dialysate. A control pump is operating that adds fluid from a control reservoir to the dialysis circuit in an influx direction via a conduit or removes fluid from the dialysis circuit to the control reservoir in an efflux direction via the conduit, and intermittently switching the control pump between the efflux direction to move fluid across the dialysis membrane from the extracorporeal circuit to the dialysis circuit and the influx direction to move fluid across the dialysis membrane from the dialysis circuit to the extracorporeal circuit, wherein the intermittent switching of the pump accomplishes the convective clearance of at least one waste species having a molecular weight less than about 66000 g/mol.

In any embodiment, a method is implemented for removing one or more impurities from a fluid and adjusting the sodium ion concentration of the fluid having the steps of measuring the conductivity of the fluid prior to entering a sorbent cartridge, dividing the fluid between a first inlet port and a second inlet port of the sorbent cartridge based upon the conductivity of the fluid, and recovering the fluid from an outlet port of the sorbent cartridge, wherein the sorbent cartridge has a first flow path connected to the first inlet port including a urease material and a second flow path connected to the second inlet port including a mixed bed anion and cation exchange material. In any embodiment, the method has additional steps of monitoring the conductivity of the fluid at an inlet end of the sorbent cartridge, monitoring the conductivity of the fluid at an outlet end of the sorbent cartridge, and calculating an amount of urea absorbed by the sorbent cartridge based at least in part upon the conductivity measured at the inlet end of the sorbent cartridge and at the outlet end of the sorbent cartridge.

In any embodiment, a system for performing kidney replacement treatment is implemented having a hemodialysis system having a controlled compliance dialysis circuit, a dialyzer with a dialysis membrane, a blood inlet end for receiving blood, a blood outlet end for allowing blood out of the dialyzer, a dialysate inlet end for receiving dialysate and a dialysate outlet end for allowing dialysate out of the dialyzer, wherein the blood and the dialysate contact different sides of the dialysis membrane; an extracorporeal circuit having a conduit for receiving blood from a subject and a conduit for returning blood to the subject and a blood pump for conveying blood from the subject, to the dialyzer and back to the subject; and a dialysis circuit having a sorbent cartridge for removing impurities or waste species from the dialysate, one or more conduits for conveying dialysate between the sorbent cartridge and the dialyzer, and a dialysate pump for conveying dialysate from the sorbent cartridge, to the dialyzer and back to the sorbent cartridge, the sorbent cartridge having a dialysate inlet end and a dialysate outlet end wherein the sorbent cartridge comprises at least one cartridge body, a first inlet port and a second inlet port and an outlet port, wherein the sorbent cartridge has a first flow path in fluid communication with the first inlet port and a second flow path in fluid communication with the second inlet port, and the first flow path having at least one interior space or sorbent material in the sorbent cartridge that is not in fluid communication with the second flow path.

In any embodiment, a sorbent cartridge containing a sorbent has a use for removing at least one impurity or waste species from an external fluid, the sorbent cartridge having at least one cartridge body having a first inlet port and a second inlet port in fluid communication with an outlet port, wherein the first inlet port defines a first flow path and the second inlet port defines a second flow path, and the first flow path having at least one interior space or sorbent material in the cartridge body that is not in fluid communication with the second flow path.

In any embodiment, a sorbent cartridge has a use in a system having a controlled compliance circuit for controlling the movement of fluid volume from the external fluid, the use including operating the system to convey the external fluid through an external circuit and a dialyzer, where the external circuit is in fluid communication with the controlled compliance circuit through a dialysis membrane housed in the dialyzer, and conveying a dialysate through the controlled compliance circuit such that the dialysate moves from the sorbent cartridge, to the dialyzer and back to the sorbent cartridge, where at least one waste species diffuses from the external fluid to the dialysate through the dialysis membrane and the sorbent cartridge substantially removes at least one impurity or waste species from the dialysate.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modification.

BRIEF DESCRIPTION OF THE DRAWINGS

FIG. 3A shows a main cartridge body and a top piece.

FIG. 3B shows a top view of the main cartridge body and the top piece. FIG. 3C shows a first molded housing. FIG. 3D shows a top view of the first molded housing. FIG. 3E shows a second molded housing and a bottom piece. FIG. 3F shows a top view of the second molded housing and the bottom piece.

FIG. 7A shows a whole device view of the sorbent cartridge holder. FIG. 7B shows a lower arm of the sorbent cartridge holder. FIG. 7C shows an upper arm of the sorbent cartridge holder. FIG. 7D shows the sorbent cartridge holder in a rinse position.

FIG. 8A shows a sorbent cartridge having two cartridge bodies. FIG. 8B shows a top view of one cartridge body of the sorbent cartridge and a top view of a top piece. FIG. 8C shows a view of a bottom piece for the one cartridge body and a bottom view for the other of the two cartridge bodies.

DETAILED DESCRIPTION OF THE INVENTION

Figure 1:
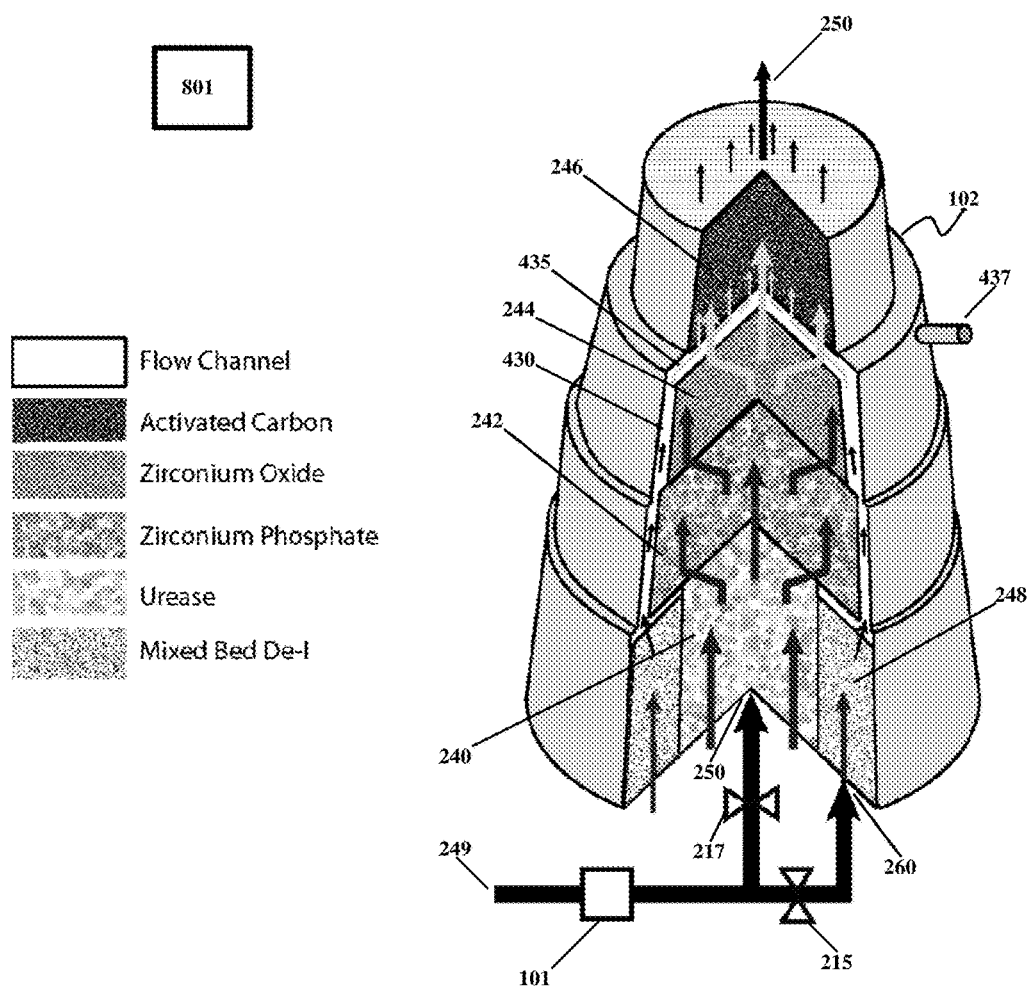
FIG. 1 shows a sorbent cartridge having first and second flow paths in accordance with certain embodiments disclosed herein.

The invention describes sorbent cartridges having at least two flow paths therein to allow for a greater fraction of the capacity of the zirconium materials to be dedicated to urea/ammonium absorption compared to cartridges having only a single flow path. The inclusion of two flow paths in the sorbent cartridge allows for the diversion of at least a portion of $Mg^{2+}$, $Ca^{2+}$ and $K^+$ present in the dialysate to be absorbed by non-zirconium materials. The lifetime of the sorbent cartridge before reaching a limit to absorb additional ammonium ions is enhanced, thereby increasing safety of the system. An increase in the useful lifespan of the sorbent cartridge is particularly advantageous in improving the safety of home-use devices without professional supervision. Further, an increase in the useful lifespan of the sorbent cartridge decreases operation costs that benefit all uses for hemodialysis.

A portable dialysis system is also described having a controlled compliance dialysis circuit. Some home-use systems employ a reservoir of working dialysis solution that varies in volume depending upon bulk movement of water across the dialysis membrane and/or water added to dilute sodium ion concentration and reduce conductivity generated during treatment. However, such systems complicate accurate control over removal of fluid from a patient through techniques such as ultrafiltration and diafiltration that are commonly employed to address fluid build-up in patients while simultaneously removing waste products from the blood. In this disclosure, a controlled compliance dialysis circuit is provided for conveying and re-circulating a dialysate in conjunction with accurate removal of the fluid volume from the patient during ultrafiltration and diafiltration. The dialysate flow path described herein has active control of fluid flow entering and exiting the flow path in a manner that allows for the accurate performance of ultrafiltration, the quantization of urea removal and the performance of convective clearance of mid-weight uremic waste species without an excessive risk for blood clotting.

Definitions

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "activated carbon" refers to a porous carbon material having a surface area greater than 500 $m^2$ per gram. Activated carbon can be capable of absorbing several species including heavy metals such as lead, mercury, arsenic, cadmium, chromium and thallium among others, oxidants such as chlorine and chloramine, fluoride ions, and waste species such as phosphate and certain nitrogen-containing waste species such as creatinine and uric acid.

The terms "administering," "administer," "delivering," "deliver," "introducing,", "bolus," and "introduce" can be used interchangeably to indicate the introduction of water or an agent into the body of a patient, including electrolytes and alkali and/or alkali earth ions, to a patient in need thereof, and can further mean the introduction of water, any agent or alkali and/or alkali earth ions to a dialysate or dialysis circuit where such water, agent or alkali and/or alkali earth ion will enter the blood of the patient by diffusion, transversal of a dialysis membrane or other means.

The term "air trap" refers to a structure for separating a gas from a mixture of a gas and a liquid. An air trap can include a hydrophobic membrane for allowing gases to pass and preventing the passage of water.

The term "anticoagulant" is a substance that prevents or delays the clotting of blood, such as heparin, fragmin, and sodium citrate.

A "biocompatible material" is a material that has the ability to interface with living biological tissues with an acceptable host response in any of specific medical systems, methods of treatment or delivery contemplated herein. The biocompatible material can consist of synthetic, natural or modified natural polymers intended to contact or interact with the biological systems during application of any of the inventions contained herein.

The term "calcium exchange resin" refers to a material that is competent to perform cation exchange by releasing calcium ions into a solution in contact with the calcium exchange resin and absorbing other cations from the solution.

The term "conduit" refers to a vessel or passageway having a void volume through which a fluid can travel or move. A conduit can have a dimension parallel to the direction of travel of the fluid that is significantly longer than a dimension orthogonal to the direction of travel of the fluid.

"Chronic kidney disease" (CKD) is a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), where the kidneys fail to function at a sufficient level.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The term "comprising" includes, but is not limited to, whatever follows the word "comprising." Thus, use of the term indicates that the listed elements are required or mandatory but that other elements are optional and may or may not be present.

The term "conductivity meter" or "conductivity sensor" refers to a device for measuring the electrical conductance of a solution.

The term "consisting of" includes and is limited to whatever follows the phrase "consisting of" Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "control pump" refers to a pump that is operable to pump fluid bi-directionally to actively control the transfer of fluid volume into or out of a compartment or circuit.

The term "control reservoir" refers to a rigid or non-rigid vessel or container accessible by the control pump that contains a variable amount of fluid.

A "control system" consists of combinations of components that act together to maintain a system to a desired set of performance specifications. The control system can use processors, memory and computer components configured to interoperate to maintain the desired performance specifications. It can also include fluid control components, and solute control components as known within the art to maintain the performance specifications.

A "controller," "control unit," "processor," or "microprocessor" is a device which monitors and affects the operational conditions of a given system. The operational conditions are typically referred to as output variables of the system, which can be affected by adjusting certain input variables.

The terms "controlled compliance" and "controlled compliant" describe the ability to actively control the transfer of fluid volume into or out of a compartment or circuit. In certain embodiments, the variable volume of fluid in a dialysate circuit expands and contracts via the control of one or more pumps. The volume of fluid in the system minus the attached reservoirs once the system is in operation is generally constant. The attached reservoirs allow the system to adjust the patient fluid volume by withdrawing fluid and storing the desired amount in an attached control reservoir and/or by providing rebalanced fluids to the patient and removing waste products. Alternatively, the fluid stored in a control reservoir attached to the dialysate circuit can be used for ultrafiltration (UF) and/or delivery of an infusate. The terms "controlled compliance" and "controlled compliant" are not to be confused with the term "non-compliant volume," which simply refers to a vessel, conduit, container, pathway or cartridge that resists the introduction of a volume of fluid after air has been removed from a defined space such as a vessel, conduit, container, pathway or cartridge.

The term "convective clearance" refers to the movement of solute molecules or ions across a semi-permeable barrier due to force created by solvent molecules moving across the semi-permeable barrier.

The term "dialysate" describes a fluid into which solutes from a fluid to be dialyzed diffuse through a membrane. A dialysate typically contains electrolytes that are close in concentration to the physiological concentration of electrolytes found in blood.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The term "dialysis membrane" can refer to a semipermeable barrier selective to allow diffusion of solutes of a specific range of molecular weights through the barrier, or optionally a high permeability membrane, which is a type of semipermeable membrane that is more permeable to water than the semipermeable membrane of a conventional hemodialysis system, which has a semipermeable membrane that has a sufficiently low permeability to water such that an ultrafiltration controller is not required to prevent excessive loss of water from the patient's blood. During high permeability hemodialysis, the system removes toxins or excess fluid from the patient's blood using the principles of convection (via a high ultrafiltration rate) and/or diffusion (via a concentration gradient in dialysate). In certain non-limiting examples, the semipermeable membrane during high permeability hemodialysis has an in vitro ultrafiltration coefficient (Kuf) greater than 8 milliliters per hour per conventional millimeter of mercury, as measured with bovine or expired human blood.

The term "diluent" refers to a fluid having conductivity less than a fluid to which the diluent is added.

The term "electrolyte" refers to an alkali or alkali earth cation dissolved in an aqueous medium.

The term "filtration" refers to a process of separating solutes from a fluid, by passing the fluid through a filter medium across which certain solutes or suspensions cannot pass. Filtration is driven by the pressure difference across the membrane.

The term "fixed volume" refers to a three-dimensional space within a vessel or container that can accommodate a maximum amount of non-compressible fluid and resist the addition of any volume of fluid above the maximum amount.

The term "fluid communication" refers to at least two fluids that are contained in compartments that are able to exchange matter, either solvent or solute molecules or ions, through a semi-permeable bather or to allow for the movement of a fluid from one defined area to another defined area through a channel, frit, etc. separating defined areas.

The terms "frit" and "spacer frit" refer to a material that is biocompatible and has a porosity between about 1 μm and 300 μm. The material can be one or more of biocompatible, compressible, an open cell polymer or foam or similar material.

The term "relative blood volume monitor" refers to any device measuring the concentration of any solute or solid material in the blood. Non-limiting examples of relative blood volume monitors include devices for measuring the concentration of oxyhemoglobin, deoxyhemoglobin, hematocrit or red blood cell count, osmolarity or total protein concentration of the blood.

The term "relative blood volume hydration status" refers to the relative change in the level of any target solute or solid material in the blood over a period of time. Non-limiting examples of target solute or solid materials include oxyhemoglobin, deoxyhemoglobin, hematocrit or red blood cell count, osmolarity or total protein concentration of the blood.

Relative blood volume hydration status can be monitored by observation of a change in a signal responsive to the level of any target solute or solid material in the blood without a requirement that the absolute concentration of the target solute or solid material be determined.

"Hemofiltration" is a therapy in which blood is filtered across a semi-permeable membrane. Water and solutes are removed from the blood via pressure-driven convection across the membrane. In hemofiltration, solutes small enough to pass through the membrane in proportion to their plasma concentration are removed. The driving force is a pressure gradient rather than a concentration gradient. A positive hydrostatic pressure drives water and solutes across the filter membrane from the blood compartment to the filtrate compartment, from which it is drained. Solutes, both small and large, get dragged through the membrane at a similar rate by the flow of water that has been engineered by the hydrostatic pressure. Hence, convection overcomes the reduced removal rate of larger solutes (due to their slow speed of diffusion) seen in hemodialysis. The rate of solute removal is proportional to the amount of fluid removed from the blood circuit, which can be adjusted to meet the needs of a clinical situation. In general, the removal of large amounts of plasma water from the patient requires volume substitution. Substitution fluid, typically a buffered solution close to the plasma water composition a patient needs, can be administered pre or post filter (pre-dilution mode, post-dilution mode).

"Hemodialysis" is a technique where blood and a "cleansing fluid" called dialysate are exposed to each other separated by a semi-permeable membrane. Solutes within the permeability range of the membrane pass while diffusing along existing concentration gradients. The dialysate employed during hemodialysis has soluble ions such as sodium, calcium and potassium ions and is not pure water. The sieving properties of the membrane exclude all solutes above a certain threshold from crossing the membrane. One common sieving property is "albumin sieving." In most situations, it is not desirable to remove Albumin during renal replacement therapy, as lower blood serum Albumin is associated with increased mortality rates. The term "albumin sieving coefficient" can be used to describe the amount of albumin that will cross the membrane.

The term "hematocrit" refers to the fraction of blood volume occupied by erythrocytes.

"Hemodiafiltration" is a therapy that combines hemofiltration and hemodialysis.

The term "impedance meter" refers to a device for measuring the opposition of an object or structure to an alternating current.

The term "infusate container" refers to a vessel, which can be rigid or non-rigid, for holding a solution of one or more salts for the adjustment of the composition of a dialysate.

The term "infusate solution" refers to a solution of one or more salts for the adjustment of the composition of a dialysate, such as salts of calcium, magnesium and potassium.

The term "impurity species" refers to a molecular or ionic species that originates from tap water, a sorbent cartridge or a source other than a patient's or subject's blood including chlorine, fluoride ions, and aluminum-containing species.

The term "nitrogenous waste" refers to any non-polymeric nitrogen-containing organic compound originating from the blood of a patient. Nitrogenous waste includes urea and creatinine.

The term "waste species" or "waste products" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system. For example, nitrogen-containing waste products are generally at a level less than 30 mg/dL in the blood for individuals with a healthy renal system and inorganic phosphate can be generally in a range between 2.5-4.5 mg/dL but not necessarily limited to this range. The level of waste products in the blood is elevated for individuals with impaired kidney function.

The term "non-compliant volume" refers to a vessel, conduit, container, pathway or cartridge that resists the introduction of a volume of fluid after air has been removed from a defined space such as a vessel, conduit, container, pathway or cartridge.

The term "oximeter" refers to a device for measuring the amount of oxygen carried by a volume of blood.

The term "luer connector" or "luer adapter" refers to adapters or connector conforming to International Standards Organization (ISO) standards 594.

The term "conical" refers to a shape for a cartridge or container that has a "tapered shape" as defined herein, wherein the diameter for a cross-section taken perpendicular to an axis of the cartridge or container, where the diameter of the cross-section changes for translation along the axis from a smaller diameter to a larger diameter or from a larger diameter to a smaller diameter.

The term "cylindrical" refers to a shape for a cartridge or container that has a substantially uniform diameter for a cross-section taken perpendicular to an axis of the cartridge or container.

The term "mesa" refers to a shape for a cartridge or container that has a "conical" or "tapered shape" as defined herein, wherein the rate of change in the diameter of a cross-section perpendicular to an axis of the cartridge or container changes at a non-constant rate for translation along the axis.

The term "memory" refers to a device for recording digital information that can be accessed by a microprocessor, such as RAM, Dynamic RAM, microprocessor cache, FLASH memory, or memory card.

The term "mid-weight uremic wastes" or "mid-weight uremic waste species" refers to substances that can pass through a dialysis membrane that have a molecular weight less than about 66000 g/mol and greater than about 1000 g/mol.

The term "moving fluid bi-directionally" refers to the ability to move a fluid across a barrier, such as a semi-permeable membrane, in either direction through the thickness of the barrier.

"Osmolarity" is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

A "patient" or "subject" is a member of any animal species, preferably a mammalian species, optionally a human. The subject can be an apparently healthy individual, an individual suffering from a disease, or an individual being treated for a disease.

The terms "pathway" and "conveyance pathway" refer to the route through which a fluid, such as dialysate or blood, travels.

The term "peristaltic pump" refers to a pump that operates by compression of a flexible conduit or tube through which the fluid to be pumped passes.

The terms "portable system" or "wearable system" refers to a system in whole or in part having a mass and dimensions to allow for transport by a single individual by carrying the system or wearing the system on the individual's body.

The terms "pressure differential" and "pressure drop" refer to the difference in pressure measurements of a fluid between two points of measurement.

The term "pressure meter" refers to a device for measuring the pressure of a gas or liquid in a vessel or container.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture with a stored program and being capable of carrying out a set of commands, automatically that can be changed or replaced.

The term "pulsatile pump" refers to a pump that mimics the action of a mammalian heart where the pumped fluid undergoes periodic variation in velocity.

The term "pump" refers to a device that causes the movement of fluids or gases by the application of suction or pressure.

The term "quick connector" refers to any structure for making an attachment that is operable by an individual using their hands or fingers without the assistance of additional tools. The quick connector can have a valve that shuts off flow when the connector is disconnected.

The term "spent dialysate" refers to a dialysate that has been contacted with blood through a dialysis membrane and contains one or more impurity or waste species or waste substance, such as urea.

The term "sorbent cartridge" refers to a cartridge containing one or more sorbent materials for removing specific solutes from solution, such as urea.

The term "sorbent material" refers to any material useful for treating the dialysate through physical contact and modifying the composition of the dialysate, including urease-containing materials, ion exchange materials and activated carbon materials.

The term "standoff" refers to a piece of molded material on an object, such as a body or housing, used to partially separate two objects that are otherwise joined together. A standoff acts as a spacer to form an open space between objects, particularly to permit the passage of a fluid.

The terms "treating" and "treatment" refer to the management and care of a patient having a pathology or condition for which administration of one or more therapeutic compounds is indicated for the purpose of combating or alleviating symptoms and complications of the condition. Treating includes administering one or more formulations of the present invention to prevent or alleviate the symptoms or complications or to eliminate the disease, condition, or disorder. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in either a dialysis, hemodiafiltration, or filtration process.

The term "void volume" refers to a specific volume that can be occupied by a fluid in a defined space such as a dialysate circuit of the invention including all components contained therein.

"Diffusive permeability" is a property of a membrane describing permeation by diffusion. Diffusion is the process of solutes moving from an area of higher concentration to an area of lower concentration The term "porosity," as used herein describes the fraction of open pore volume of a membrane.

The term "shunt," as used herein describes a passage between channels, such as blood vessels, where the shunt diverts or permits flow from one pathway or region to another.

The term "plumbing," as used herein generally describes any system of valves, conduits, channels, and lines for supplying any of the fluids used in the invention.

The term "extracorporeal," as used herein means situated or occurring outside the body.

The term "effluent dialysate," as used herein describes the discharge or outflow after the dialysate has been used for dialysis.

The term "metabolic waste species," as used herein describes organic and inorganic components generated by a patient. They can be metabolic products such as urea, uric acid, creatinine, chlorides, inorganic sulfates and phosphate, or excess electrolytes such as sodium, potassium, etc. It will be understood that the specific "metabolic waste species" can vary between individuals depending on diet and environmental factors. Hence, the term is intended to encompass any waste component that is normally removed by a kidney or by dialysis without restriction on the specific type of waste substance.

The term "working dialysate solution" refers to a dialysate solution that is undergoing active circulation or movement through a system including conduits, pathways, dialyzers and cartridges.

Sorbents for Dialysis Regeneration

Dialysate eluted from a dialyzer employed during hemodialysis therapy contains waste species, such as urea that entered the dialysate from the blood. The dialysate can further contain impurities introduced into the dialysate from a sorbent cartridge or by the introduction of tap water. The sorbent cartridge removes these impurities and waste species prior to reuse of the refreshed dialysate. Sorbent materials that can perform removal of waste species and impurities and regenerate the dialysate for use in the controlled compliance dialysis circuit are known. Examples of useful sorbent materials include the REDY sorbent system. The sorbent cartridge typically contains four different kinds of materials as follows: 1) a urease-containing material, where urease is an enzyme that catalyzes the conversion of urea to ammonia (ammonium ions) and carbon dioxide; 2) a zirconium phosphate (ZrP) material that has the capacity to act as a cation exchanger by absorbing a large quantity of ammonium ions in exchange for sodium and hydrogen ions, where the ZrP material also exchanges $Mg^{2+}$, $Ca^{2+}$ and $K^+$ ions for sodium and hydrogen ions; 3) a zirconium oxide material (ZrO), which acts as an anion exchanger by exchanging phosphate for acetate and bicarbonate; and 4) an activated carbon material that has a surface area for absorption of a wide range of impurities and waste species including metal ions and mid-weight uremic waste species, such as B12, C reactive protein and β2-microglobin and other waste species such as uric acid and creatinine. Examples of useful sorbent materials include the REDY sorbent system and U.S. Pat. Nos. 3,669,880; 3,989,622; 4,581,141; 4,460,555; 4,650,587; 3,850,835; 6,627,164; 6,818,196; and 7,566,432 and U.S. Patent Publications 2010/007838; 2010/0084330; and 2010/0078381, and International Patent Publication WO 2009/157877 A1, which are incorporated herein by reference.

Dual Flow Sorbent Cartridge

A typical sorbent cartridge passes dialysate entering the cartridge through the urease-containing material, the ZrP material, the ZrO material and the activated carbon material in that order. Some sorbent cartridges can contain an additional activated carbon material that contacts the used dialysate prior to the urease-containing material to remove metal ions or fluorine ions that can damage the urease-containing material. Similarly, a single activated carbon material can also be placed prior to the urease-containing material such that the activated carbon material is the first material contacted by dialysate entering the column. In some embodiments the zirconium phosphate can be replaced with magnesium phosphate, as magnesium phosphate.

The sorbent cartridge of the invention acts as a cation exchanger to absorb ammonia ions and other cations (e.g. $K^+$, $Ca^{2+}$, and $Mg^{2+}$) in exchange for releasing sodium ions and hydrogen ions in a stoichiometric fashion. Urea is converted to ammonia and carbon dioxide by a urease-containing material in the sorbent cartridge. Due to the slightly basic pH of the dialysate, ammonia is present as ammonium ions. A portion of the carbon dioxide generated by the urease-containing material is converted to carbonic acid by hydrolysis. The ammonium ions are exchanged for sodium and hydrogen in the zirconium phosphate layer(s) of the sorbent cartridge. The stoichiometry of the amount of sodium given off in this exchange is dependent on the processing of the zirconium phosphate layer; however, each process provides uniform results. By means of example, a representative example of the zirconium phosphate material can operate to exchange 1 mEq ammonium ion for 0.15 mEq sodium ion and 0.85 mEq hydrogen ion.

Zirconium phosphate has a tendency to absorb all cations, including ammonium ions over $K^+$, $Ca^{2+}$, and $Mg^{2+}$ ions, present in the dialysate passing over the zirconium phosphate material. Zirconium phosphate is employed in hemodialysis applications due to its molecular sieving properties and its ability to absorb large amounts of ammonium ions compared to other cation exchange materials. Zirconium phosphate is an expensive material that constitutes a significant portion of the cost of the non-renewable sorbent cartridge. Less expensive cation exchange materials are known; however, those materials have an inferior ability to absorb ammonium ions compared to zirconium phosphate. Exhaustion of zirconium phosphate by absorption of cations can lead to ammonium ion breakthrough, where non-absorbed ammonia is eluted from the sorbent cartridge, which can be extremely hazardous to the patient. Although safety systems to detect ammonium ion breakthrough can be incorporated into the system, any potential for ammonium ion breakthrough is a safety risk. Therefore, extension of the operating life of the sorbent cartridge improves safety of the system as well as reducing cost.

Disclosed herein are sorbent cartridges having two flow paths incorporated in a single cartridge body or assembly. A first flow path passes dialysate entering an inlet of the cartridge though a urease-containing material, a zirconium phosphate material, a zirconium oxide material and an activated carbon material; the order of the sorbent materials of the first flow path can be modified. A second flow path passes dialysate entering an inlet of the sorbent cartridge through a mixed anion and cation de-ionization resin (mixed bed de-I resin) and an activated carbon material. The mixed bed de-I resin is employed to absorb sodium ions from the dialysate, where sodium ion concentration has a tendency to increase over a course of treatment. Concurrently, the mixed bed de-I resin serves to absorb at least a portion of the $K^+$, $Ca^{2+}$, and $Mg^{2+}$ ions that would otherwise decrease the ammonium-absorption capacity of the sorbent cartridge. The sorbent cartridge can be used to decrease the conductivity of the dialysate while simultaneously reducing the use of the zirconium phosphate material for purposes other than ammonium ion absorption.

Without adjustments, sodium ion concentration will increase to unsafe levels over the course of treatment due primarily to the function of the zirconium phosphate material to exchange ammonium ions, as well as $K^+$, $Ca^{2+}$, and $Mg^{2+}$, for sodium and hydrogen ions. The normal constituents of the dialysate is $Na^+$ from 137 to 142 mEq/L, $K^+$ from 1 to 4 mEq/L, $Ca^{2+}$ from 2 to 3 mEq/L, $Mg^{2+}$ from 0.5 to 1 mEq/L and $HCO_3^-$ from 32 to 40 mEq/L. There is also typically a small amount of dextrose in the solution. Sodium ions ($Na^+$) are the major ionic content of dialysis solution in the standard dialysate composition. To gain an estimate of the magnitude of sodium ions added to the dialysate over the course of treatment, exchange of 10 grams urea for a daily therapy would result in the subsequent exchange of ammonium for sodium equal to about 180 mEq of sodium. The further exchange of $Ca^{2+}$, $Mg^{2+}$ and $K^+$ results in the production of about 240 mEq sodium.

The absorption of $Ca^{2+}$, $Mg^{2+}$ and $K^+$ ions consumes a greater amount of the capacity of the sorbent cartridge than absorption of ammonium ions generated from urea. As such, diversion of a portion of the $Ca^{2+}$, $Mg^{2+}$ and $K^+$ contained in the dialysate from absorption by the zirconium phosphate material can significantly increase the amount of ammonium ions absorbed by the sorbent cartridge during its operational life and decrease the likelihood of ammonium ion breakthrough before cartridge replacement. Using the example from above, reduction of the amount of $Ca^{2+}$, $Mg^{2+}$ and $K^+$ absorbed by the zirconium phosphate material by 10% will allow for the capacity of the zirconium phosphate material to absorb ammonium ions to increase by approximately 13%.

Exemplary Dialysis Flow Path

Figure 2:
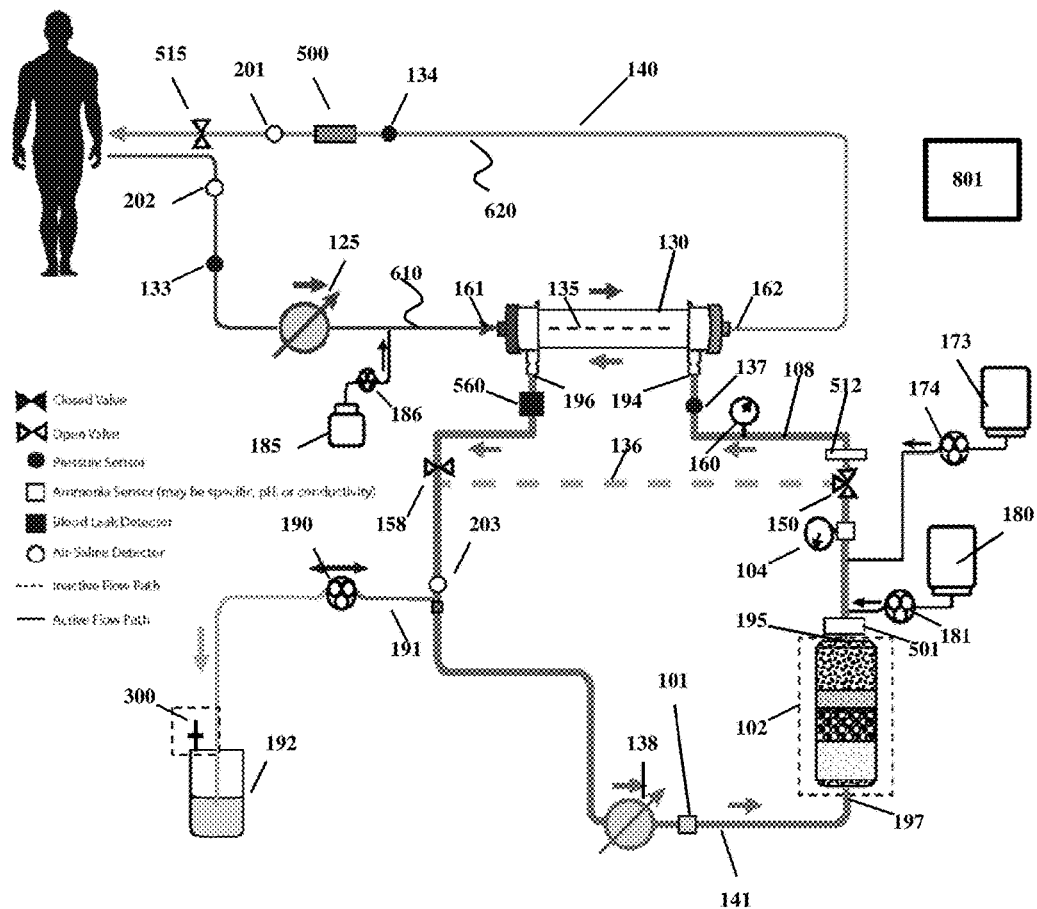
FIG. 2 shows a hemodialysis device having a controlled compliant dialysis circuit operating in accordance with certain embodiments.

FIG. 1 shows a sorbent cartridge 102 in accordance with certain embodiments disclosed herein. A conductivity meter 101 measures the conductivity of the dialysate prior to entry to the sorbent cartridge 102 at inlet 197 (FIG. 2). Conductivity is monitored by controller 801 that controls the actuation of one or more valves 215 and 217. In certain embodiments, only one valve, 215 or 217, can be present and/or one of valves 215 and 217 can be a three-way valve. One or more of valves 215 and 217 direct dialysate entering the sorbent cartridge 102 from a conduit 249 to travel either a first flow path 250 or a second flow path 260 through the sorbent cartridge 102. In certain embodiments, valve 215 is present and valve 217 is not present in the system.

Before discussion of additional structure details of the sorbent cartridge 102, an exemplary hemodialysis system having a controlled compliant flow path will be described. Those skilled in the art will recognize that the cartridge of FIG. 1 can be used in any appropriate system. FIG. 2 shows a system and flow path for circulating blood and a dialysate through a dialyzer 130. A shunt, such as a needle or catheter, is connected to a patient's vasculature to draw blood and circulate the patient's blood through an extracorporeal circuit 140. Access to the shunt can be controlled by a valve 515. The portion of the extracorporeal circuit 140 that contains drawn blood from the patient can be referred to as the arterial line 610, which by convention is understood to mean a line for transporting blood from the patient regardless of whether blood is drawn from an artery or vein of the patient. The portion that returns blood to the patient can be referred to as the venous line 620. In certain embodiments, the arterial line 610 and the venous line 620 connect with one or more veins of the patient. Locomotive power for moving the blood through the extracorporeal circuit 140 is provided by a blood pump 125, which is typically located along the arterial 610 line. Blood is typically conveyed through the extracorporeal circuit 140 at a rate of 50 to 600 mL/min and can be adjusted by a controller 801 to any required rate suitable for a procedure performed by the invention. Blood pump 125 can be a peristaltic pump, although those skilled in the art will readily understand that other types of pumps can be used, including diaphragm pumps, centrifugal pumps, and shuttle pumps. In certain embodiments, blood pump 125 is not a pulsatile pump.

In certain embodiments, the blood pump 125 conveys blood through the dialyzer 130 where the blood is contacted with a blood side of a high permeability dialysis membrane 135. Blood enters the dialyzer 130 through a blood inlet 161 and exits through a blood outlet 162. The pressure of the blood prior to the dialyzer 130 is measured by a pressure meter 133 and post dialyzer 130 by a pressure meter 134. The pressure at pressure meter 133 gives an indication of the adequacy of the blood flow into the circuit, increased vacuum is an indication of a less adequate access flow. The pressure indication at pressure meter 134 indicates obstructions in the venous bloodline 620. An air trap 500 is placed along the extracorporeal circuit 140 to prevent the introduction of air into the circulatory system of the patient. The air trap 500 is not limited to a particular design. Typical air traps employ a hydrophobic membrane that allows air to be separated from an air-liquid mixture by allowing air to pass through the membrane and retaining water-based fluids. Alternatively the air trap may be run full and the pressure sensor uses a flexible impermeable membrane to transmit pressure pulses to the pressure transducer so there is no direct air blood interface. Air-fluid detectors 201 and 202 are present to confirm that air is not present in the extracorporeal circuit 140. Air-fluid detectors 201 and 202 can be ultrasonic sensors that can detect a change in solution density or scattering due the presence of air or air bubbles. A valve 515 can be present to control access to the subject's vascular system.

During the course of conveyance of blood along the extracorporeal circuit 140, heparin or a similar anticoagulant is added to the blood to prevent clotting of blood within the dialyzer 130 or blood conveyance pathway/extracorporeal circuit 140. Heparin or another anticoagulant is added from an anticoagulant container 185 at a metered rate using an anticoagulant pump 186. The anticoagulant pump 186 can be any pump capable of accurately metering heparin. Alternatively, a surface of the extracorporeal circuit 140 can be covalently bound to heparin or another anticoagulant.

Dialysate within the system is conveyed through one of a first dialysate pathway 108 in the dialysate circuit 141, which carries dialysate to the dialyzer 130, or a second bypass pathway 136 shown in a dashed line, which serves to bypass the dialyzer 130. The first and second pathways 108 and 136 have one or more conduits for conveying the dialysate. Access to the second bypass pathway 136 is controlled by valve 150. It is understood by one skilled in the art that three-way valve 150 can be replaced with a two-way valve with the same result to control the flow through the dialyzer 130 or bypass pathway 136. The first dialysate pathway 108, the second bypass pathway 136, and residual volume in the dialyzer 130 including conduits for conveying the dialysate together form a dialysis circuit 141 that houses the circulating volume of the dialysate present in the system.

Dialysate that is conveyed through the dialyzer 130 on the dialysate side of the dialysis membrane 135 picks up waste species from the blood, including urea, by diffusion, hemofiltration or hemodiafiltration. Dialysate enters the dialyzer 130 at a dialysate inlet end 194 and exits at an outlet end 196. The dialysate exiting the dialyzer 130 passes through a blood leak detector 560 that can determine the presence of blood in the dialysate indicating a breach in the dialysis membrane 135. Flow of dialysate from the dialyzer 130 can be stopped or controlled through the operation of valve 158. Valve 158 can also be operated to prevent the backup of dialysate into the dialyzer 130. The dialysate is conveyed through a sorbent cartridge 102 to remove waste species before being re-conveyed through the dialyzer 130. Any impurities that may be present are also removed from the dialysate by the sorbent cartridge 102. The dialysate enters the sorbent cartridge 102 at a dialysate inlet end 197 and exits at an outlet end 195. An air trap 501 is positioned after outlet end 195 to remove gasses introduced into the dialysate by the sorbent cartridge 102. The volume of actively circulating dialysate or working dialysate solution is determined by the total void volume of the conduits and the sorbent cartridge 102 forming the dialysis circuit 141. The void volumes of the conduits and of the sorbent cartridge 102 forming the dialysis circuit 141 have a substantially inflexible volume. In certain embodiments, the dialysis circuit 141 has a void volume from about 0.15 to about 0.5 L. In other embodiments, the dialysis circuit 141 has a void volume from about 0.2 to about 0.4 L or from 0.2 to about 0.35 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 to about 5 L, and micro-volumes from as small as 0.1 to about 0.5 L such as 0.1 to 0.2, 0.1 to 0.3, 0.1 to 0.4, 0.2 to 0.3, 0.3 to 0.4, or 0.3 to 0.5 L are contemplated by the invention.

The controlled compliance dialysis circuit has two points where fluid can enter the dialysate flow path: 1) infusate pumps and 2) a control pump that controls the movement of fluid across the dialysis membrane. The controlled compliance dialysis circuit operates by employing two principal components: 1) an extracorporeal circuit that is attached to the vasculature and the circulation of a patient, and 2) a dialysis circuit having a limited void volume for the circulation of a dialysate. The extracorporeal circuit is an extension of the patient's circulatory system external to the patient's body. Any fluid added to the dialysis circuit 141 will enter the patient's body; likewise, any fluid drawn out of the extracorporeal circuit 140 originates from the patient's body. Due to the connection between the extracorporeal circuit 140 and the vascular system, there is freedom of movement for fluid to flow into and out of the extracorporeal circuit due to the relatively large volume of the patient's body to accommodate an influx of fluid or to serve as a reservoir for fluid. As will be described in greater detail below, a control pump 190 is employed to actively control fluid movement between the extracorporeal circuit 140 and the dialysis circuit 141. This capability is used to enhance the convective clearance of the system while controlling the net fluid removed from the patient.

The total void volume of the conduits having a substantially inflexible volume prevents the passive inflow and outflow of fluid volume due to pressure changes that can occur over the course of treatment. This is beneficial because not all pressure changes during treatment are under precise control by a user or operator. A controlled compliance dialysis circuit is achieved by actively controlling the inflow (influx) and outflow (efflux) of fluid to and from the dialysis circuit 141 and the extracorporeal circuit 140. In this manner, the volume of fluid crossing the dialysate membrane 135 is under direct control and can be accurately determined. In certain embodiments, the dialysis circuit 141 has a void volume from about 0.15 to about 0.5 L. In other embodiments, the dialysis circuit 141 has a void volume from about 0.2 to about 0.4 L or from 0.2 to about 0.35 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 to about 5 L, and micro-volumes from as small as 0.1 to about 0.2 L are contemplated by the invention.

In particular, the controlled compliance dialysis circuit can be accurately controlled to precisely remove or add fluid to the dialysis circuit 141. Due to the substantially inflexible void volume of the conduits, the sorbent cartridge 102 and other components of the dialysis circuit 141, the net movement of fluid over any time interval across the dialysis membrane 135 can be accurately controlled by creating a means to accurately introduce or remove fluid from the patient.

The controlled compliance dialysis circuit also has an advantageous feature in that the movement of fluid across the dialysis membrane 135 can be controlled without affecting the flow rate of dialysate entering the dialyzer 130.

As shown in FIG. 2, the dialysate is moved along the dialysis circuit 141 by a dialysate pump 138. When the control pump 190 is not operating, fluid along the length of the dialysis circuit 141 flows at a rate determined by the dialysate pump 138. When the control pump 190 is operating, fluid exiting the dialyzer 130 and traveling toward the conduit 191 is flowing at rate that is the combination of the rates of the control pump 190 and the dialysate pump 138. However, the fluid traveling from the entry point of conduit 191 into the dialysis circuit 140 to the dialyzer 130 is traveling at the rate of the dialysate pump 138. As such, the rate of fluid traveling to the dialyzer 130 is not affected by the operation of the control pump 190. The dialysate pump can be operated at a rate from about 10 to about 400 mL/min, the specific rate being dependent on the rate of the blood pump 125 at the desired contact time with the dialysis membrane 135 to achieve diffusion of impurities from blood to the dialysate. The rate of the dialysate pump 138 and the blood pump 125 can be controlled by a controller 801.

Refreshed dialysate exiting an outlet end of the sorbent cartridge 102 can be monitored by a conductivity meter 104 and/or a conductivity meter 160. Necessary electrolytes are added to the refreshed dialysate from a reservoir 180 having an infusate solution by an infusate pump 181. The point at which the infusate (i.e. cation) solution is added to the dialysate can be between the sorbent cartridge 102 and the valve 150 in certain embodiments or between the sorbent cartridge 102 and the dialysate inlet 194 of the dialyzer 130 in other embodiments. The design of any conductivity meter employed in embodiments described herein is not particularly limited; however, a typical conductivity meter has two electrodes where a current between the two electrodes is monitored. The presence of sodium ions in the dialysate is the major contributor to the conductivity measured by conductivity meter 104. Conductivity is continually monitored and reported to the controller 801 to assess the quality and safety of the dialysate. When the conductivity of the dialysate falls within a predetermined range, the dialysate is directed by valve 150 to a dialysate inlet end 194 of the dialyzer 130; the valve 150 is located between an outlet end 195 of the sorbent cartridge 102 and the dialysate inlet end 194 of the dialyzer 130. In certain embodiments, the valve 150 is a three-way valve. Optionally, the dialysate can be filtered through a microbial filter 512. The pressure of the dialysate entering the dialysate inlet end of the dialyzer 130 is measured by a pressure meter 137. In certain embodiments, the predetermined range for the conductivity of the dialysate is from about 12.6 to about 15.4 mS/cm.

When the conductivity measured by meter 104 and/or 160 is outside of the predetermined range, the valve 150 directs the dialysate to be conveyed through the second dialysis flow path 136 shown as a dashed line. Further, valve 158 can be closed to prevent the dialysate from backing up into the dialyzer 130. As such, the dialysate can be circulated through the sorbent cartridge 102 while bypassing the dialyzer 130 and preventing contact with the patient's blood when required. Since the dialysis circuit 141 is isolated from the extracorporeal circuit 140 when valve 158 is closed, the control pump 190 is not operated when valve 158 is in a closed position during normal operation. When the system is being initially primed to replace air in the extracorporeal circuit 140 and dialysate circuit 141 with fluid, control pump 190 can operate to vent air from the dialysis circuit 141.

Due to the substantially inflexible void volume of the conduits and the sorbent cartridge 102, bulk fluid or water is prevented from moving from across the membrane 135 from the extracorporeal circuit 140 of the dialyzer 130 to the dialysate circuit 141 of the dialyzer 130. Specifically, due to the substantially inflexible void volume of the dialysis circuit 141, water cannot passively move from the extracorporeal side to the dialysate side through the dialysis membrane. In the event of factors that tend to increase pressure on the extracorporeal side of the dialysis membrane, such as increase blood flow rate or blood viscosity, pressure across the membrane will automatically be equalized due to the limited volume of the dialysis circuit 141 and the non-compressible nature of the dialysate. In the event of factors that tend to increase pressure on the dialysate side of the dialysis membrane 135, such as increased dialysis flow rate, net movement of water from the dialysis circuit 141 to the extracorporeal circuit 140 is prevented by a vacuum that would form in the dialysis circuit 141 in the event of such a movement. Since the dialyzer is a high flux type there is some fluid flux back and forth across the dialyzer membrane due to the pressure differential on the blood and dialysate sides of the membrane. This is a localized phenomenon due to the low pressure required to move solution across the membrane and is called backfiltration, however results in no net fluid gain or loss by the patient.

Using the controlled compliance dialysis circuit described herein, net movement of water across the dialysis membrane occurs under active control rather than passively due to pressure differences that develop across the dialysis membrane due to normal operations. A control pump 190 is present and accesses the controlled compliance dialysis circuit 141 through a conduit 191. In certain embodiments, the conduit 191 joins with the controlled compliance dialysis circuit 141 at a point upstream from the dialyzer 130. The compliance control pump 190 can be operated in an influx direction that moves fluid from a control reservoir 192 to the controlled compliance dialysis circuit 141 or in an efflux direction that moves fluid from the controlled compliance dialysis circuit 141 into the control reservoir 192. Due to the substantially inflexible volume of the dialysis circuit 141, volume added to the controlled compliance dialysis circuit when the compliance control pump 190 operates in the influx direction causes net movement of fluid from the dialysate side of the dialysis membrane 135 to the extracorporeal side of the dialysis membrane 135. When the compliance control pump 190 is operated in the efflux direction, fluid is drawn from the extracorporeal side of the dialysis membrane into the controlled compliance dialysis circuit. In certain embodiments, the compliance control pump 190 can be operated at a rate from 0 to about 200 mL/min in either direction. In certain other embodiments, the control pump 190 can be operated at a rate from 0 to about 100 mL/min or 0 to 50 mL/min in either direction. Any range from about 0 to about 200 mL/min is contemplated by the invention such as about 15 to about 185 mL/min, about 25 to about 175 mL/min, about 5 to about 75 mL/min, about 61 to about 183 mL/min, about 156 to about 193 mL/min, about 32 to about 63 mL/min, about 145 to about 199 mL/min, about 16 to about 93 mL/min or, about 29 to about 124 mL/min.

In embodiments where the control pump 190 is operated in the influx direction, the dialysate pump 138 operates at a rate higher than the control pump 190 to prevent flow of the used dialysate back into the dialyzer 130. The dialysate pump 138 functions to convey the dialysate from the point where line 191 joins the dialysis circuit 141 to the sorbent cartridge 102. A rate of the dialysate pump 138 operating faster than the control pump 191 in the influx direction ensures that the contents of the control reservoir 192 are conveyed to the sorbent cartridge 102 and do not reach the dialyzer 130 without first passing through the sorbent cartridge. In certain embodiments, the dialysate pump 138 operates at a rate that is about 100 mL/min greater and at rates greater than the rate of the control pump 190, when the control pump 190 is operating in the influx direction. For example, if the rate of the control pump 190 is 10 mL/min, the dialysate pump 138 can operate at rates greater than about 110 mL/min such as 130 mL/min, 175 mL/min, 210 mL/min, 510 mL/min, 760 mL/min, 1 L/min, and 1.6 L/min. If the rate of the control pump 190 is 25 mL/min, the dialysate pump 138 can operate at rates greater than about 125 mL/min such as 130 mL/min, 175 mL/min, 210 mL/min, 510 mL/min, 760 mL/min, 1 L/min, and 1.6 L/min. In one embodiment, the dialysate pump 138 operates at a rate that is about 20 mL/min greater and at rates greater than the rate of the control pump 190 or higher, when the control pump 190 is operating in the influx direction. In other embodiments, the dialysate pump 138 operates at a rate that is about twice the rate and at rates greater than that of the control pump 190, when the control pump 190 is operating in the influx direction. In certain embodiments, the dialysate pump 138 operates at a rate that is about 5% higher and at rates higher than the rate of the control pump 190, when the control pump 190 is operating in the influx direction. For example, the dialysate pump 138 can operate at 6%, 7%, 8%, 10%, 15%, 45%, 63%, 75%, 100%, 200%, 500%, 2000%, or any higher percentage than the rate of the control pump 190.

The control reservoir 192 is not limited to any particular structure. In certain embodiments, the control reservoir 192 can be made from a flexible or collapsible material that expands depending on the volume held. In certain embodiments, the control reservoir 192 can be substantially inflexible. The control reservoir 192 can include a hydrophobic 0.2 micron (μm) sterile, non-pyrogenic, and non-toxic air filter 300 to prevent the entry of bacteria or endotoxin into the control reservoir 192 and dialysis circuit 141. The air filter 300 also sterilizes air exhaust and intake from the control reservoir 192 into the system. Further, the air filter 300 can release air pressure present in the control reservoir 192. The material of air filter 300 may be Millipore Duale™ filter or an equivalent known to one of ordinary skill. In certain embodiments, the control reservoir 192 can have a valve that allows the patient or subject to empty the volume of the control reservoir 192 without interrupting treatment.

Several sensors and monitors can be employed to determine the state of the dialysis system, as shown in FIG. 2. Blood leaks across the dialysis membrane 135 can be detected by a blood leak detector 560. The blood leak detector 560 can be an optical detector having a light source and photo detector allowing for the observation of a red color in the dialysate. The presence of air or fluid in the extracorporeal circuit 140 and dialysis circuit 141 can be determined by air-fluid detectors 201, 202, and 203, which can be ultrasonic sensors that can detect a change in solution density or scattering due to the presence of air or air bubbles. Conductivity meters 101, 104 and 160 can be present to monitor the composition of the dialysate within the dialysis circuit. Pressure meters 133, 134 and 137 can be present to determine an unsafe operating pressure and/or fluid leak from the system. The pressure meter can be a transducer device that operates through capacitive or piezoelectric principles to convert the amount of force applied to a surface to an electronic signal.

Ultrafiltration (UF) and Increased Convective Clearance

The compliance control pump 190 is operated by a controller 801 that accurately accounts for the volume of fluid being removed from the circulation of the patient and/or being infused into the circulation of the patient. As described above, the compliance control pump 190 controls the movement of fluid across the dialysis membrane 135 due to the substantially inflexible volume of dialysis circuit 141. Many kidney failure patients can have fluid build-up that may be addressed by ultrafiltration, where bulk fluid is removed via the circulatory system. The compliance control pump 190 can be accurately used to determine the precise volume of fluid removed from the patient. In addition to accurately controlling the net fluid removed and the convective clearance of a patient, accurate control of the efflux or influx of fluid via the compliance control pump 190 allows for the amount of sodium removed (mEq Na$^+$) during a course of treatment to be determined, where such result can be calculated and stored in the memory of a controller 801 and/or be displayed on a control panel (not shown). Accurate control of bulk fluid movement across the dialysis membrane can further be used to enhance clearance of mid-weight impurities by convective clearance, which is particularly beneficial for mid-weight impurities such as β-2 which are not removed very well by hemodialysis and which higher serum blood levels are associated with higher patient mortality. To be able to control net patient fluid removal, any fluid removed in excess of the desired patient fluid loss must be reinfused to the blood. This is accomplished in one embodiment by running the control pump 190 in reverse during the treatment and then compensating by ultrafiltration: Control Pump Control=Net patient UF+Convective UF. Control pump backfiltration is controlled to Convective UF volume. For example, a desired 200 ml net patient fluid loss per hour and 1000 ml of convection per hour requires a control pump 190 running at a UF rate (efflux rate) of 1000 ml/hr and at a backfiltration rate (influx rate) of 800 ml/hr to achieve the net fluid loss and the desired convective clearance. These same mechanisms allow one to give fluid to the patient when necessary, rinse back blood and control fluid removal accurately.

The rate of diffusion of a solute is dependent upon the molecular weight of that solute. Small molecule waste species, such as urea, can effectively diffuse from the extracorporeal side of the dialysis membrane to the dialysate side of the dialysis membrane in the absence of net movement of fluid. However, larger, mid-sized molecules, having a lower rate of diffusion may not be removed as effectively. As used herein, the term mid-sized molecule or mid-sized uremic waste species refers to an impurity having a molecular weight less than about 66000 g/mol and greater than about 1000 g/mol and includes uremic toxins, B12, C reactive protein and β2-microglobin.

During periods of net movement of fluid from the extracorporeal side to the dialysate side of the dialysis membrane 135, solutes can be dragged across the dialysis membrane 135 along with the net movement of fluid. This process, referred to as convective clearance, removes mid-weight waste species from the patient's blood, which are absorbed by the sorbent cartridge 102. Some convective clearance occurs during the course of ultrafiltration as described above. However, the amount of convective clearance is limited by the volume of fluid that is removed by ultrafiltration. For example, if 1 L of fluid is to be removed from the patient over the course of a 4-hour treatment, then the amount of convective clearance that occurs due to 1 L of fluid crossing the dialysis membrane 135 is the maximum amount of convective clearance that occurs during the treatment regimen. Without infusing the patient with additional fluid, the amount of fluid that can be removed is limited considering that the average individual has about 5 L of blood. Further, it may be desirable to achieve convective clearance without the removal of a large amount of fluid from the patient.

To achieve convective clearance in accordance with certain embodiments, the control pump 190 is operated in the efflux direction to pull fluid from the extracorporeal circuit 140, and hence from the patient, across the dialysis membrane 135. During the net efflux for fluid across the membrane 135, mid-weight uremic waste species are carried into the circulating dialysate where they can be absorbed by the sorbent cartridge 102. The control pump 190 is periodically reversed to the influx direction to force fluid from the control reservoir 192 into the controlled compliance dialysis circuit 141 and thereby force a corresponding volume of fluid into the extracorporeal circuit 140 and into the patient.

Under a regime where the control pump 190 is run in the efflux and influx directions for approximately equal amounts of time at the same pump rate, the amount of convective clearance will be approximately the efflux flow rate without causing any net addition or removal of fluid from the patient. For example, if the compliance control pump 190 is run at 10 mL/min for a hour with periodic reversal between efflux and influx directions, then 300 mL of fluid is moved from the extracorporeal circuit into the controlled compliance dialysis circuit 141 to affect convective clearance, where the same volume is returned to the patient resulting in no net fluid removal at the end of treatment. In the alternative, the time that the compliance control pump 190 is operated in the efflux or influx direction can be unequal to affect a net volume of ultrafiltration during the course of treatment. For example, if the control pump 190 is operated in the efflux direction for 18-second periods with intervening 12-second periods in the influx direction at a rate of 10 mL/min, then 360 mL/h of fluid is moved in the efflux direction to affect convective clearance and a net of 120 mL/h of fluid is removed from the patient. Those skilled in the art will understand that the interval at which the control pump 190 operates between efflux and influx directions can be modified to further effect the amount of convective clearance and net ultrafiltration occurring over the course of treatment.

The blood pump 125 and the dialysate pump 138 provide the majority of the energy to convey the blood through the extracorporeal circuit 140 and the dialysate through the controlled compliance dialysis circuit 141, respectively. In certain embodiments, the blood pump and the dialysate pump can be independently operated at any rate in a range from about 50 to about 300 mL/min including from about 60 to about 295 mL/min is contemplated by the invention such as about 76 to about 185 mL/min, about 85 to about 287 mL/min, about 25 to about 115 mL/min, about 45 to about 273 mL/min, about 156 to about 293 mL/min, about 32 to about 163 mL/min, about 145 to about 199 mL/min, about 167 to about 193 mL/min or, about 29 to about 224 mL/min. In certain embodiments, the blood pump and/or the dialysate pump deliver a constant load pressure such that the conveyance rate is constant over at least short periods of times. Pumps that can deliver a constant load pressure include peristaltic pumps.

The use of pulsatile pumps, that mimic the pulsing action of the human heart, has been proposed to enable convective clearance. As discussed herein, in known devices, the blood and the dialysate are conveyed by pulsatile pumps that are set 180 degree out of phase in order to achieve periodic filtering across the dialysis membrane. When the blood pump is undergoing a pulse action and the dialysate pump is at rest, convective clearance can occur due to an increase in pressure difference across the dialysis membrane. Conversely, fluid is back filtered across the dialysis membrane when the dialysate pump is undergoing a pulse action and the blood pump is at rest. However, such systems have been subject to increased clotting. It is desirable to stop the administration of heparin or other anticoagulant 30 to 60 minutes prior to the end of dialysis to restore normal clotting by the time treatment ends. However, blood becomes significantly more viscous at low flow rates. In addition, protein coats the membrane surface starting the clotting cascade. The periodic slow down of blood circulation caused by the action of a pulsatile pump contributes to clotting occurring in the extracorporeal circuit. Blood clotting prevents the completion of treatment.

The above-described method for performing convective clearance using pulsatile pumps requires the flow rate of the blood and the dialysate through the dialyzer to be similar to function properly. The pressure generated in the dialyzer on either side of the dialysis membrane is dependent upon the flow rate, where the flow rate of the dialysate and the blood should be close to achieve equal movements of fluid in both directions across the dialysis membrane. Specifically, the ratio of blood flow to dialysis flow has been recommended to be from 3:4 to 4:3 when employing pulsatile pumps to increase convective clearance. The use of pulsatile pumps to perform convective clearance also increases hemoconcentration, which increases the risk for blood clotting. As the flow rate of blood through a dialyzer is lowered relative to the flow rate of dialysate through the dialyzer, any particular volume of fluid pulled from the extracorporeal circuit during a unit value of time causes a greater amount of hemoconcentration. That is, the volume of fluid removed from the extracorporeal circuit is removed from a smaller volume of blood as the flow rate of blood is lowered. As described above, a ratio of blood flow to dialysis flow has been recommended to be from 3:4 to 4:3 when pulsatile pumps are used to create convective clearance. Using the controlled compliance dialysis circuit described herein, the net flux of fluid across the dialysis membrane 135 is controlled by the control pump 190 rather than a ratio of flow rates between blood and dialysate. As such, the ratio of blood flow to dialysate flow can be set at a value that reduces hemoconcentration as a result of pulling fluid from the extracorporeal circuit. In certain embodiments, the ratio of blood flow to dialysate flow through the dialyzer 130 is from about 1:1.5 to 3:1, and can include any range of ratios in between. In certain other embodiments, the rate of blood flow through the dialyzer 130 is at least about 50% greater than the rate of dialysate flow through the dialyzer 130.

As shown in FIG. 2, a second reservoir 173 and second reservoir pump 174 can be present in any embodiment of the systems described herein. As described above, the control pump 190 can be operated in a bidirectional fashion to assist in the performance of convective clearance. Specifically, the control pump can be operated in the efflux direction to cause the movement of fluid from the extracorporeal circuit 140 into the dialysis circuit 141 and in the influx direction to cause the movement of fluid from the dialysis circuit 141 into the extracorporeal circuit 141.

In certain embodiments, operation of the control pump 190 in the influx direction can be substituted with operation of the second reservoir pump 174 to drive liquid from the second reservoir 173 into the dialysis circuit 141 and subsequently cause movement of fluid from the dialysis circuit 141 to the extracorporeal circuit 140 across the dialysis membrane 135. The control pump 190 can be used for the movement of fluid in the opposite direction across the dialysis membrane 135. The second reservoir pump 174 and second reservoir 173 is used for the performance of convective clearance in embodiments of the invention where the total void volume of the dialysis circuit and working dialysate is less than about 0.5 L, or in embodiments where the void volume of the dialysis circuit and working dialysate is less than 1 L.

The second reservoir 173 can hold water, tap water or purified water. As discussed, the exchange of ammonium ions by the sorbent cartridge 102 has a tendency to release sodium ions into the dialysate. While the concentration of sodium ions in the dialysate can be reduced through the operation of the control pump 190 in the efflux direction, diversion of the dialysate through the deionization cartridge 210 or polystyrene sulfonate cartridge 250, these routes to reduction sodium ion concentration in the dialysate may potentially not be sufficient to reduce sodium ion concentration. As such, the second reservoir pump 174 can be operated to add water or another fluid as a diluent to the dialysis circuit 141 to reduce sodium concentration as needed.

In certain embodiments, the volume of fluid held by the second reservoir 173 is about 1 L or less, or about 0.5 L or less. In certain embodiments, the volume of the fluid held by the reservoir is from about 0.1 to about 1 L, from about 0.2 to about 0.8 L, from about 0.5 to about 1 L, from about 0.6 to about 1 L, from about 0.5 to about 0.8 L or from about 0.2 to about 0.8 L.

Dual Flow Sorbent Cartridge

FIG. 1 shows a sorbent cartridge 102 in accordance with certain embodiments disclosed herein. As shown in FIG. 2, a conductivity meter 101 measures the conductivity of the dialysate prior to entry to the sorbent cartridge 102 at inlet 197. Referring to FIG. 1, the conductivity of the dialysate measured by conductivity meter 101 (or 104 or 160 of FIG. 2) is monitored by controller 801 that controls the actuation of one or more valves 215 and 217. In certain embodiments, only one valve, 215 or 217, can be present and/or one of valves 215 and 217 can be a three-way valve. One or more of valves 215 and 217 direct dialysate entering the sorbent cartridge 102 from a conduit 249 from the dialysate circuit to travel either a first flow path 250 or a second flow path 260 through the sorbent cartridge 102. In certain embodiments, valve 215 is present and valve 217 is not present in the system.

Dialysate traveling the first flow path 250 contacts a urease-containing material 240, a zirconium phosphate material 242, a zirconium oxide material 244, and an activated carbon material 246. Those skilled in the art will readily understand that the order in which the dialysate conveyed through the first flow path 250 comes into contact with various sorbent materials can be different from the order presented in FIG. 1. In certain embodiments, an additional activated carbon layer can be located along the first flow path 250 before the urease-containing material 240, which can remove heavy metals and/or fluoride ions that can damage the urease-containing material 240. Similarly, the activated carbon material 246 can be located before the urease-containing material 240 on the first flow path 250. In certain embodiments, dialysate that is conveyed along the first flow path 250 does not come into contact with a mixed bed deionization material that contains both anion and cation exchange materials.

Dialysate traveling the second flow path 260 contacts at least two sorbent materials: 1) a mixed bed deionization material 248; and 2) an activated carbon material 246. In certain embodiments, the activated carbon material 246 in the first flow path 250 and the second flow path 260 can be the same material. That is, the activated carbon material 246 is shared between the first flow path 250 and the second flow path 260. Fluid entering the first flow path 250 and fluid entering the second flow path 260 are distinct at the point of entering the sorbent cartridge 102 at an inlet. However, fluid directed through the first flow path 250 and fluid directed through the second flow path 260 can mix and/or pass through the same compartment or interior space at locations within the sorbent cartridge 102 upstream from an inlet.

When the conductivity of the dialysate is within a predetermined range, the dialysate is directed by either valve 215 and/or valve 217 through the first flow path 250 of the sorbent cartridge 102. As the conductivity of one or more of conductivity meters 101, 104, and/or 160 registers a conductivity above the desired predetermined range, a portion of the total dialysate flow through the sorbent cartridge 102 can be diverted through the second flow path 260. The mixed bed de-I material 248 contains a cation exchange material that absorbs cations, such as sodium ions, from the dialysate and releases hydrogen ions, and an anion exchange material that absorbs anions, such as chloride ions, from the dialysate and releases hydroxide ions. As such, the effluent from the second flow path 260 is substantially deionized purified water and has a low conductivity. In an exemplary sorbent cartridge, the dialysate flow from the first flow path 250 and the dialysate flow from the second flow path 260, having a low conductivity, recombine at an outlet end 195, shown in FIG. 2, of the sorbent cartridge 102. As such, the dialysate flow through the second flow path 260 acts as a diluent to reduce the conductivity of the effluent of the sorbent cartridge 102 and hence adjusts the conductivity of the dialysate circulating in the dialysis circuit 141. The division of dialysate flow between the first flow path 250 and the second flow path 260 can be controlled by one or more controllers 801. In certain embodiments, the predetermined range of conductivity is from about 12.6 to about 15.4 mS/cm. If needed, fluid from the second control reservoir 173 can be added to the dialysis circuit 141 to control conductivity.

The materials useful for forming the mixed bed de-I material 248 are relatively inexpensive in comparison with zirconium-containing materials. As described, substantially all non-sodium and non-ammonium cations, such as $Mg^{2+}$, $Ca^{2+}$ and $K^+$, are removed from the dialysate by the sorbent cartridge 102 regardless of whether the dialysate is conveyed though the first 250 or the second 260 flow paths. All cations, including sodium, passing through the second flow path 260 are removed by the mixed bed de-I material 248, which reduces the load on the zirconium phosphate material 242. A portion of the urea present in the dialysate passing through the second flow path 260 is removed by the activated carbon material 246. Due to the ability of the mixed bed de-I material to form a substantially deionized diluent, a relatively low fraction of the total dialysate flow through the sorbent cartridge 102 is required to be conveyed through the second flow path 260 during normal operation to maintain a stable conductivity of the dialysate. In certain embodiments, about 20% or less of the dialysate flow through the sorbent cartridge 102 is through the second flow path 260 and about 80% or more of the dialysate flow is through the first flow path 250. In certain additional embodiments, about 10% or less of the dialysate flow through the sorbent cartridge 102 is through the second flow path 260 and about 90% or more of the dialysate flow is through the first flow path 250, or about 5% or less of the dialysate flow through the sorbent cartridge 102 is through the second flow path 260 and about 95% or more of the dialysate flow is through the first flow path 250. As such, a large portion of urea is removed from the dialysate passing through the sorbent cartridge 102 by either by the action of the urease-containing material 240 and the zirconium phosphate material 242 in the first flow path 250 or absorption by the activated carbon material 246 in the second flow path 260. Any residual urea present in the effluent of the sorbent cartridge 102 does not pose a safety danger to the patient.

As shown in FIG. 1, the sorbent cartridge 102 can have an optional side port 437 present for the addition of a bicarbonate solution. As discussed, the zirconium phosphate material releases hydrogen ions into solution that has a tendency to lower pH. As such, the dialysate and the patient tend to become acidic as treatment progresses. Further, the zirconium oxide material can absorb bicarbonate ions from solution, although the zirconium oxide material can become a source of bicarbonate ions when saturated with bicarbonate. As shown in FIG. 1, the side port 437 can be present at a position to allow a bicarbonate salt to be added directly to the second flow path 260 and potentially bypass the zirconium oxide material. The bicarbonate salt is added to the dialysate under the control of a controller in order to maintain the concentration of bicarbonate ion within predetermined ranges. A bicarbonate solution can be metered at a constant rate to maintain a stable pH within the dialysate. In the alternative, a pH meter can be co-located with any of conductivity meters 101, 104 and/or 160 to monitor the pH of the dialysate and the rate of bicarbonate addition to the port 437 adjusted accordingly. In other embodiments, the level of bicarbonate ions can be determined by a change in conductivity since bicarbonate salts are conductive. Bicarbonate ions can be unstable in the presence of certain cations such as calcium ions. The bicarbonate solution is concentrated at the point of addition to the dialysis circuit 141 which increases instability. As such, addition of the bicarbonate solution through side port 437 decreases the instability of the bicarbonate ions since no calcium ions are present in the second flow path 260 after contact with the mixed bed de-I material. Alternatively, the bicarbonate solution can be added at another point along the dialysis circuit 141.

Sorbent Cartridge Embodiments

Figure 3A:
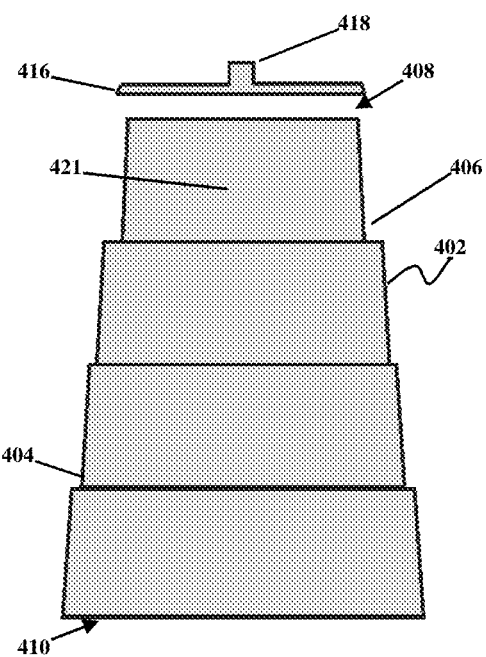
FIGS. 3A through 3F shows components for forming a sorbent cartridge having first and second flow paths within one cartridge body in accordance with certain embodiments disclosed herein.

With reference to FIGS. 3A through 3F, an embodiment of a sorbent cartridge 102, as shown in FIG. 2, having a first flow path 250 and second flow path 260, as shown in FIG. 1, will be described. As shown in FIG. 3A, a cartridge body 402 is provided that houses components and sorbent materials forming the sorbent cartridge 102. The cartridge body 402 has a top portion 406 and a bottom portion 404, where the top portion 406 and the bottom portion 404 have sidewalls. One or more sidewalls of the cartridge body 402 define a downstream opening 408 of the cartridge body 402 and an upstream opening 410 of the cartridge body 402. As used herein, the term "downstream" refers to a component located toward the direction where a fluid exits the sorbent cartridge 102 through an outlet, and the term "upstream" refers to a component located toward the direction where a fluid enters the sorbent cartridge 102. The top portion 406 and the bottom portion 404 of the cartridge body 402 are defined as the half-way point in terms of distance between the downstream opening 408 and the upstream opening 410, where the downstream 408 and upstream 410 openings are substantially parallel. The cartridge body 402 can have a tapered shape, which is herein defined as the cartridge body 402 having a larger mean diameter for the bottom portion 404 of the cartridge body 402 compared with the top portion 406 of the cartridge body 402. A portion of the interior of the cartridge body 402 adjacent to the downstream opening 408 severs as a first interior space for holding a sorbent material. The cartridge body 402, including the upper portion 406 and the lower portion 404, has a height dimension ("h"), which is defined as the direction perpendicular to the parallel downstream 408 and upstream 410 openings. The mean diameter is defined by Formula (I), where $D_h$ is the length of the longest imaginary line that can be drawn on a cross-section of the cartridge body 402 perpendicular to the dimension "h." The length of dimension h for the feature being measured is divided into 100 arbitrary length units h for purposes of determining the mean diameter.

$$MeanDiameter = \frac{\sum_{h=o}^{100} D_h}{100} \quad (I)$$

Figure 3B:
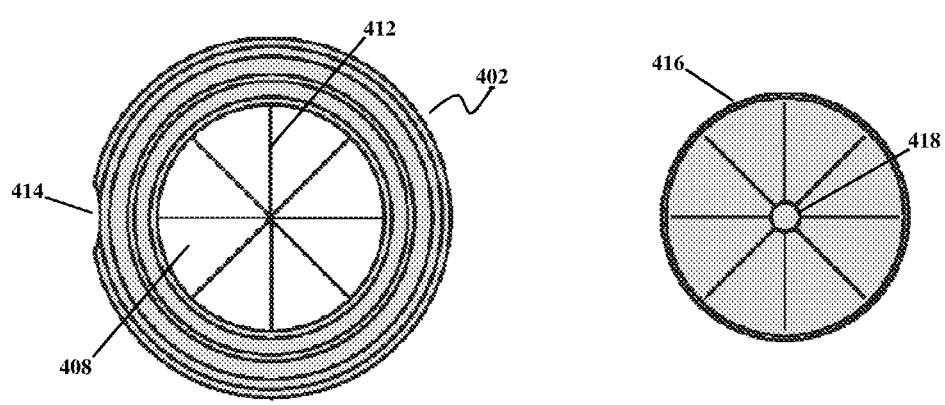

FIG. 3B shows a top view of the cartridge body 402 and the downstream opening 408. One or more support bars 412 can optionally be present to cross the downstream opening 408 to assist in retaining sorbent materials and other components within the cartridge body 402. As shown in FIG. 3B, an alignment notch 414 can be formed in the cartridge body 402 to assist with the orientation of internal components. Also shown in FIG. 3B is a top piece 416 having an outlet port 418 for allowing fluid to exit the cartridge body 402. The top piece 416 is molded to the cartridge body 402 at the downstream opening 408 to seal the sorbent cartridge 102.

Figure 3C:
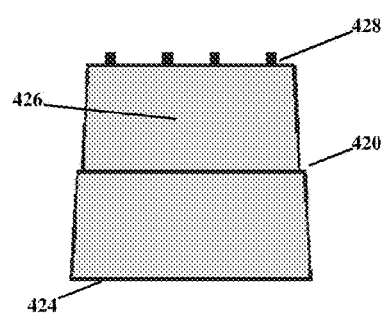

FIG. 3C shows a first molded housing 420 having a second interior space 426 formed from one or more sidewalls of the first molded housing 420. The first molded housing 420 has a downstream opening 422 and upstream opening 424 formed by the one or more sidewalls of the first molded housing 420. The first molded housing 420 fits within the cartridge body 402 such that a first flow channel 430, as shown in FIG. 1, is formed between the one or more sidewalls of the first molded housing 420 and one or more sidewalls of the cartridge body 402. When placed in the cartridge body 402, the first interior space 421 is formed within the cartridge body 402 between the downstream opening 422 of the first molded housing 420 and the downstream opening 408 of the cartridge body 402. The first molded housing 420 can have a tapered shape similar to the cartridge body 402, where the molded housing can be divided into a top portion and a lower portion. The dimensions of the first molded housing 420 and the cartridge body 402 are selected such that the first molded housing 420 cannot be inserted into the cartridge body 402 to the point of reaching the downstream opening 408.

Figure 3D:
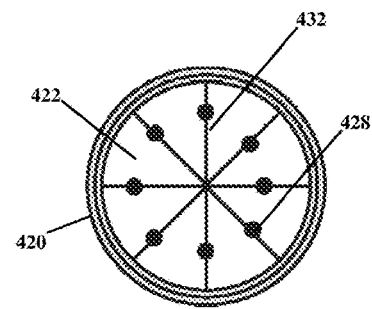

FIG. 3D shows a top view of the first molded housing 420. A plurality of standoffs 428 project from the top surface of the first molded housing 420. A plurality of support bars 432 can be present to assist in retaining sorbent materials and other components within the first molded housing 420. The standoffs 428 project in a direction perpendicular to the plane of the downstream opening 422 from a base surface that can be either one or more of the support bars 432 or a molded lip surrounding the downstream opening 422.

Figure 3E:
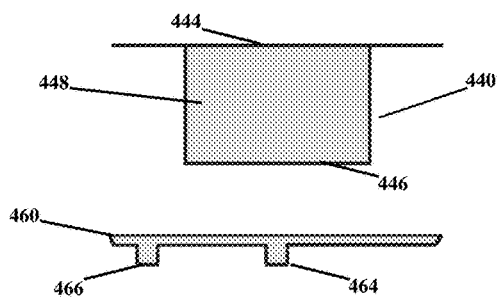
Figure 3F:
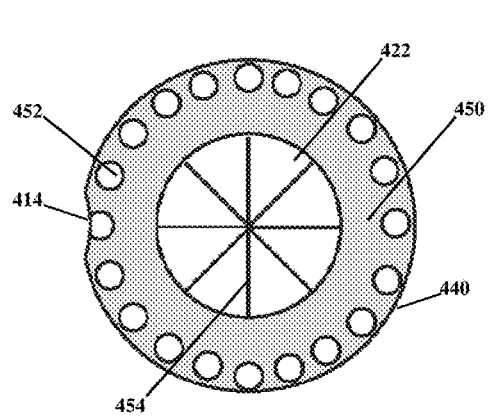
Figure 3F:
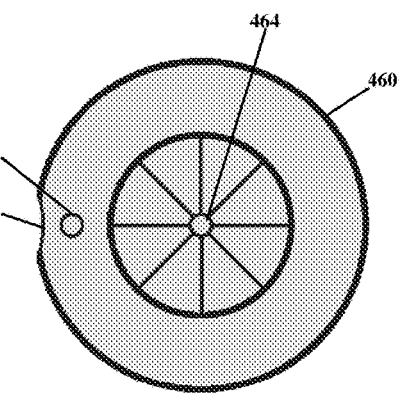

FIG. 3E shows a second molded housing 440 having one or more sidewalls defining a downstream opening 444 and an upstream opening 446. The interior of the second molded body 440 defines a third interior space 448. FIG. 3F shows a top view of the second molded housing 440, where an annular peripheral portion 450 is formed around the downstream opening 444. The annular peripheral portion 450 has a plurality of openings 452 that are in fluid communication with the first flow channel 430, shown in FIG. 1. In certain embodiments, the annular peripheral portion 450 is not formed in a circular or elliptical shape; the descriptor annular refers to the peripheral portion 450 surrounding the downstream opening 444. A plurality of support bars 454 can be present to assist in retaining sorbent materials and other components within the second molded housing 440.

When placed within the sorbent cartridge body 402, the annular peripheral portion 450 makes contact with the one or more sidewall of the sorbent cartridge 402. A space between the one or more sidewalls of the second molded housing 440 and the cartridge body 402 defines a fourth interior space 456, shown in FIG. 5, within the cartridge body 402.

The bottom of the cartridge body 402 is sealed with a bottom piece 460, as shown in FIG. 3F. The bottom piece 460 has a recess 462 (FIG. 4) located on the interior side of the bottom piece 460 having approximately the same shape and dimensions as the upstream opening 446 of the second molded body 440 such that the second molded housing 440 fits within the recess 462, shown in FIGS. 5 and 6. A first input port 464 and a second input port 466 are formed on the exterior surface of the bottom piece 460. The first input port 464 is in fluid communication with the third interior space 448 and the second input port 466 is in fluid communication with the fourth interior space 456, shown in FIG. 5.

Figure 4:
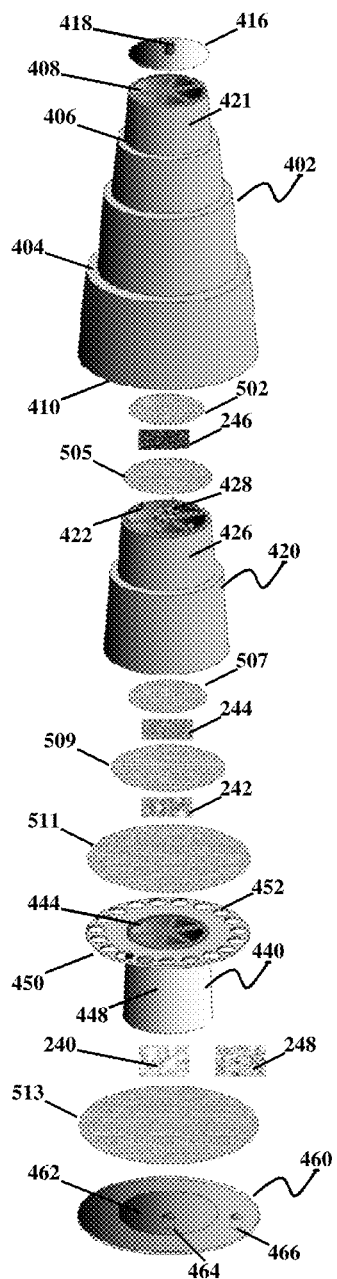
FIG. 4 shows the assembly of components for forming a sorbent cartridge having first and second flow paths within one cartridge body in accordance with certain embodiments disclosed herein.

FIG. 4 illustrates the assembly of the structures shown in FIGS. 3A through 3F to form a sorbent cartridge 102, shown in FIGS. 1 and 2. The top of FIG. 4 shows the cartridge body 402 and top piece 416, while arranged below the cartridge body 402 are internal components in order of their arrangement in the cartridge body 402. Spacer frits 502 and 505 are placed in the second interior space 426 of the cartridge body 402. The spacer frit 502 is placed at the downstream opening 408 and a substantial portion of the first interior space 421 is filled with a sorbent material, such as an activated carbon material 246. The spacer frit 505 is placed to hold the sorbent material within the first interior space 421 in place and with proper compression. The first molded housing 420 is placed within the cartridge body 402 such that the standoffs 428 contact the spacer frit 505. A spacer frit 507 is placed within the first molded housing 420 at the downstream opening 422 of the first molded housing 420. One or more sorbent materials can be placed within the second interior space 421. Each sorbent material placed in the second interior space 426 can be separated by a spacer frit. As shown in FIG. 4, a zirconium oxide material 244 and zirconium phosphate material 242 can placed in the second interior space 421 separated by a spacer frit 509. The bottom portion of the first molded housing 420 can then be secured with spacer frit 511 to secure the sorbent material within the first molded housing 420.

In certain embodiments, sorbent materials can be intermixed and placed within the same interior space without any separation. In certain embodiments, the urease-containing material and the zirconium phosphate material are intermixed in the same interior space within the sorbent cartridge 102. The urease-containing material can be immobilized or covalently linked to a substrate material. The substrate material is not particularly limited, where suitable substrate materials include organic polymers, carbohydrate-based polymers, polyamides, polyesters, inorganic polymeric materials, chitosal and silica gel. The inclusion of the urease-containing material and the zirconium phosphate material in the same interior space can improve workability of the sorbent materials to prevent clogging of the sorbent cartridge 102 or improve absorption of ammonium ions by the zirconium phosphate material. In certain embodiments, the intermixed urease-containing material and zirconium phosphate material can be place in more than one interior space. In particular, the intermixed urease-containing material and zirconium phosphate material can be present in the second interior space 421 and/or the third interior space 448.

Upon placement of the first molded housing 420 within the cartridge body 402, the standoffs 428 rest against the spacer frit 505, which is present at the bottom of the first interior space 421 of the cartridge body 402. Due to the presence of the standoffs 428, a space is formed between the first molded housing 420 and the sorbent material present in the first interior space 421. This space serves as the second flow channel 435, shown in FIG. 1, for the first flow path 250 and second flow path 260, also shown in FIG. 1. Further, a space is formed between the one or more sidewalls of the first molded housing 420 and the one or more sidewalls of the cartridge body 402, which serves as the first flow channel 430, shown in FIG. 1. The first flow channel 430 and the second flow channel 435 are in fluid communication and can form a contiguous space through which fluid can flow.

The second molded housing 440 forms a third interior space 448 for holding a sorbent material. In certain embodiments, the urease-containing material 240 is present in the third interior space 448. The annular peripheral portion 450 surrounding the downstream opening 444 of the second molded housing 448 contacts the one or more sidewalls of the cartridge body 402 when placed within the cartridge body 402. The remaining portion of the second molded housing 440 sidewalls form a space between the second molded housing 440 and the one or more sidewalls of the cartridge body 402 to create a fourth interior space 456, shown in FIG. 5. In certain embodiments, mixed bed de-I resin 248 is placed within the fourth interior space 456 as shown in FIG. 5.

When placed within the cartridge body 402, the second molded housing 440 is located between spacer frit 511 and spacer frit 513, both of which have a sufficient diameter to contact the sidewalls of cartridge body 402. The bottom of the cartridge body 402 is sealed with bottom piece 460 such that the second molded housing 440 fits within recess 462 of the bottom piece 460. Input port 464 formed on the bottom piece 460 is in fluid communication with the third interior space 448 and input port 466 is in fluid communication with the fourth interior space 456, shown in FIG. 5.

Figure 5:
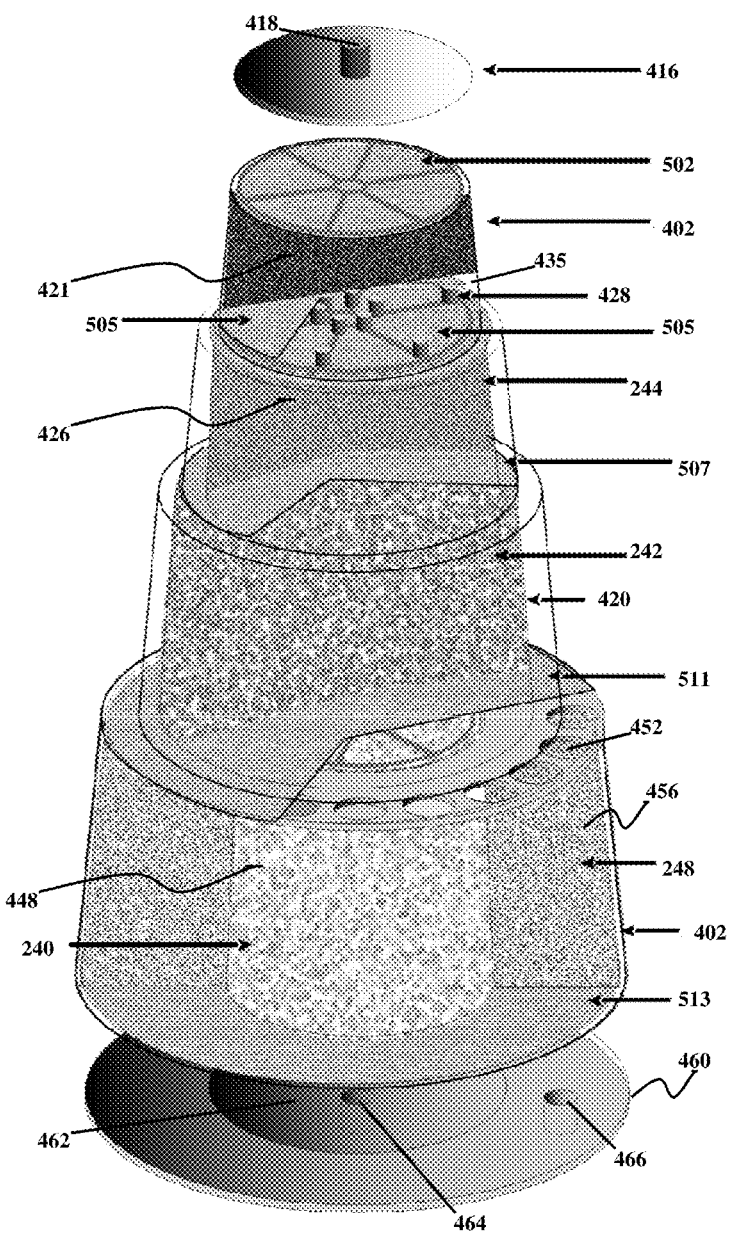
FIG. 5 shows a cutaway view of a sorbent cartridge having first and second flow paths within one cartridge body in accordance with certain embodiments.

An exemplary assembled sorbent cartridge 102 is shown in FIG. 5 with cutaways to show internal components. A fluid introduced into the first inlet port 464 passes into the third internal space 448 followed by the second internal space 426. As shown, the second internal space 426 is divided by spacer frit 509, shown in FIG. 4, to accommodate two sorbent materials. Optionally, the third internal space 448 and/or the fourth interior space 456 can be divided to contain two or more sorbent materials by insertion of an additional spacer frit (not shown). In particular, an activated carbon material can be placed as a second sorbent material in the third 448 and/or fourth 456 interior spaces to absorb impurities that can be found in tap water prior to reaching other materials with the sorbent cartridge 102.

As shown in FIG. 5, the first flow path 250, shown in FIG. 1, is formed by fluid entering the sorbent cartridge 102 at inlet port 464 and being conveyed through third interiors space 448, second interior space 426, second flow channel 435 and first interior space 421, and then exiting the sorbent cartridge at outlet port 418. The second flow path 260 shown in FIG. 1 is formed by fluid entering the sorbent cartridge 102 at inlet port 466, shown in FIGS. 3 through 5, and being conveyed through fourth interior space 456, shown in FIG. 5, first flow channel 430, shown in FIG. 1, second flow channel 435, shown in FIGS. 1 and 5, and then exiting at outlet port 418, shown in FIGS. 3 through 5. As shown, several components and internal compartments of the sorbent cartridge 102 are shared between the first flow path 250, shown in FIG. 1, and second flow path 260, shown in FIG. 1, which allow the fluid entering the inlet ports 464 and 466, shown in FIGS. 3 through 5, to be combined into a single effluent from the sorbent cartridge at outlet port 418. In particular, the first interior space 421 and the second flow channel 435 are shared between the first flow path 250 and the second flow path 260 in the embodiment shown in FIG. 5.

Those skilled in the art will readily understand that the embodiment of a sorbent cartridge shown in FIG. 5 can readily be modified to alter the order of the first flow path 250 and second flow path 260 shown in FIG. 1. For example, the standoffs 428 can be placed on a surface of the second molded housing 440 such that a flow channel (not shown) is located between the first 420 and second 440 molded housings. In such an arrangement, the second interior space 426 will additionally be shared by the first 250 and second 260 flow paths. Those skilled in the art will readily understand that additional modifications to the sorbent cartridge 102 can be made. A feature of the sorbent cartridges disclosed herein is that the first flow path has at least one interior compartment that is not in fluid communication with the second flow path. A further feature of the sorbent cartridges disclosed herein is that the second flow path has at least one interior compartment that is not in fluid communication with the first flow path.

The spacer frits present in the sorbent cartridge serve to compress the sorbent materials to have satisfactory flow characteristics. The taper shape of the sorbent cartridge 102 is also present to promote good flow characteristics. In certain embodiments, the spacer frits compress a sorbent material with a pressure from about 1 to about 100 psi. In certain other embodiments, the spacer frits compress a sorbent material with a pressure from about 10 to about 75 psi. In certain other embodiments, the spacer frits compress a sorbent material with a pressure from about 10 to about 50 psi or from about 5 to about 35 psi.

Integration of Sorbent Cartridge

As shown in FIG. 2, the sorbent cartridge 102 is placed in the conveyance flow path of the dialysis circuit 141 such that fluid from the conduits making up the dialysis circuit 141 enters the sorbent cartridge 102 at an inlet end 197 and exits the sorbent cartridge 102 at an outlet end 195. As shown in FIG. 1, a conduit 249 from the dialysis circuit 141 can be split into the first flow path 250 and the second flow path 260 by the means of valve 215 and/or 217. The sorbent cartridge can be attached to conduit 249 through any suitable connector or fastener, such as a luer adapter to integrate the sorbent cartridge 102 the system. Optionally, a detector, such as a pressure switch-type detector, a magnetic switch, or an optical detector, can be present to determine the connection state of any connector described herein.

Figure 6:
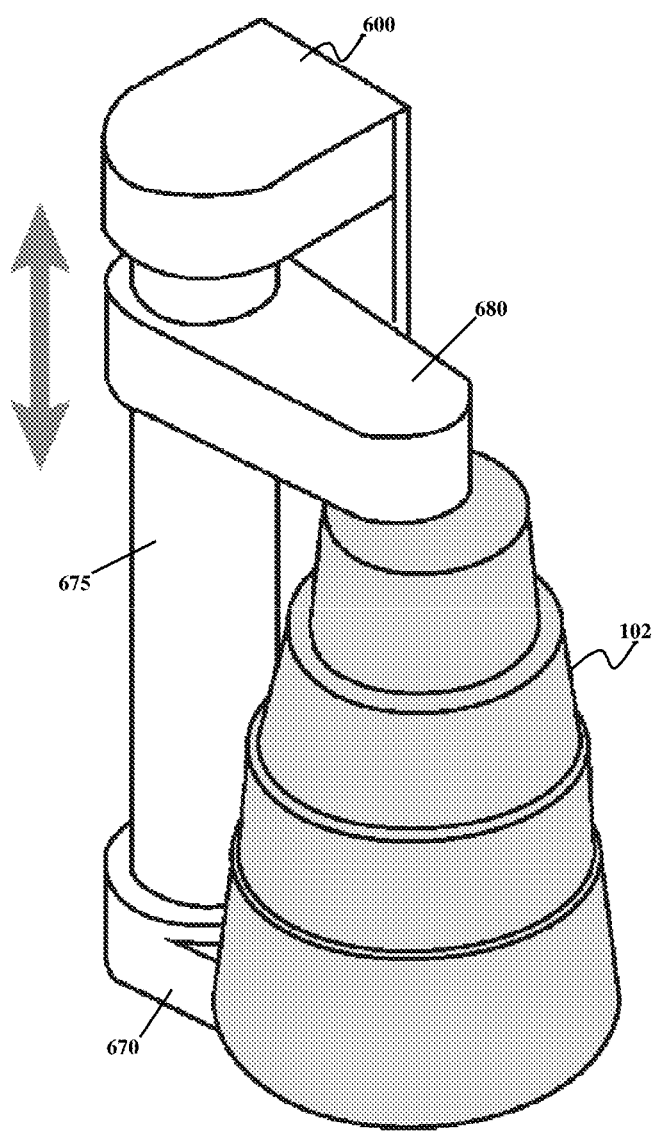
FIG. 6 shows an embodiment sorbent cartridge in a sorbent cartridge holder.

Alternatively, the sorbent cartridge can be placed in a holder 600, as shown in FIG. 6. The holder 600 has an upper arm 680 and a lower arm 670 that are substantially parallel. At least one of arm 670 and arm 680 is moveable alone a support shaft 675 that has a longest dimension that is substantially perpendicular to the longest dimensions of arms 670 and 680. The arm 680 accesses the outlet port 418 of the sorbent cartridge 102 and arm 670 accesses the first 464 and second 466 input ports.

Figure 7A:
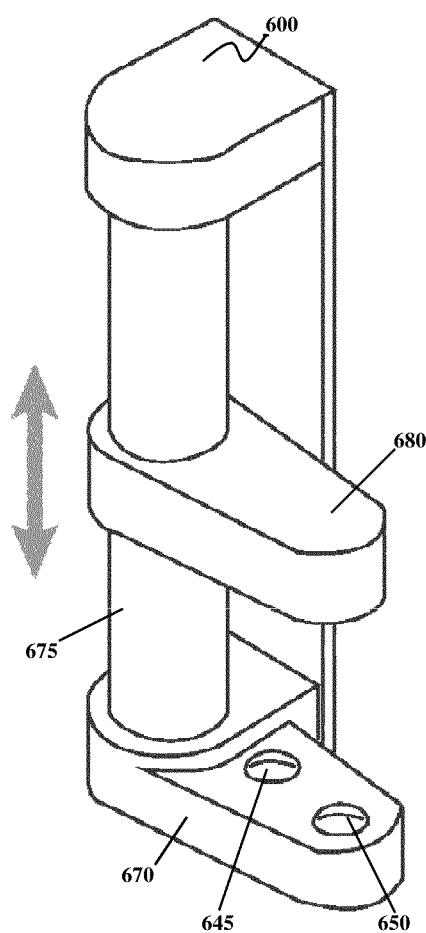
FIGS. 7A through 7D shows an embodiment sorbent cartridge holder.

FIGS. 7A through 7D show the holder 600 in greater detail without a sorbent cartridge present. FIG. 7A shows the adjustability of the upper arm 680 to assume an intermediate position along the support shaft 675, which allows the holder to accommodate sorbent cartridges of varying sizes. The lower arm 670 has two access terminals 645 and 650 that align with the a first and a second input port of a sorbent cartridge, for example inlet ports 464 and 466 as shown in FIGS. 3 through 5. A conduit (not shown) from a dialysis circuit enters the lower arm 670. In certain embodiments, one or more components can be housed within the lower arm 670, for example conductivity meter 101, valve 215 and valve 217 shown in FIG. 1. Access terminal 645 carries fluid flow for a first flow pathway, such as the first flow pathway 250 shown in FIG. 1, while access terminal 650 carries fluid flow for a second flow pathway, such as the second flow pathway 260 shown in FIG. 1.

Figure 7B:
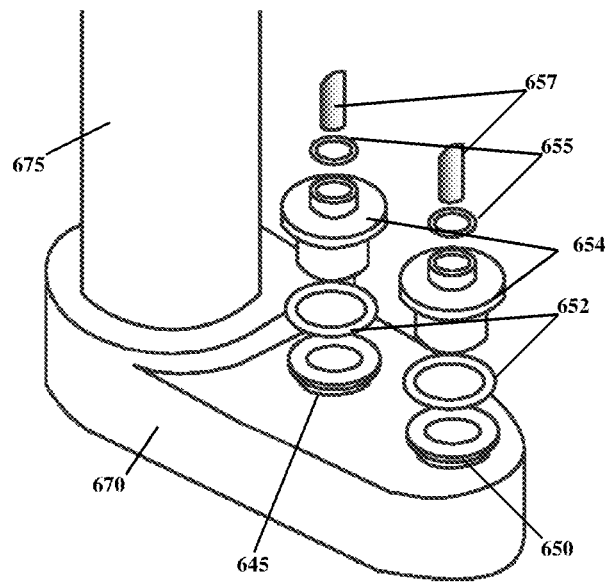

As shown in FIG. 7B, the access terminals 645 and 650 on the lower arm 670 are presented in more detail. Each of the access terminals 645 and 650 has a main terminal body 654 for interfacing with inlet ports of a sorbent cartridge, such as inlet ports 464 and 466 shown in FIGS. 3 through 5. An o-ring 652 creates a leak-free seal between sorbent cartridge inlets and access terminals 645 or 650. A male adapter piece 657 is present to contact sorbent cartridge inlet ports with o-ring 655 present to form a tight seal with the access terminals 645 or 650.

Figure 7C:
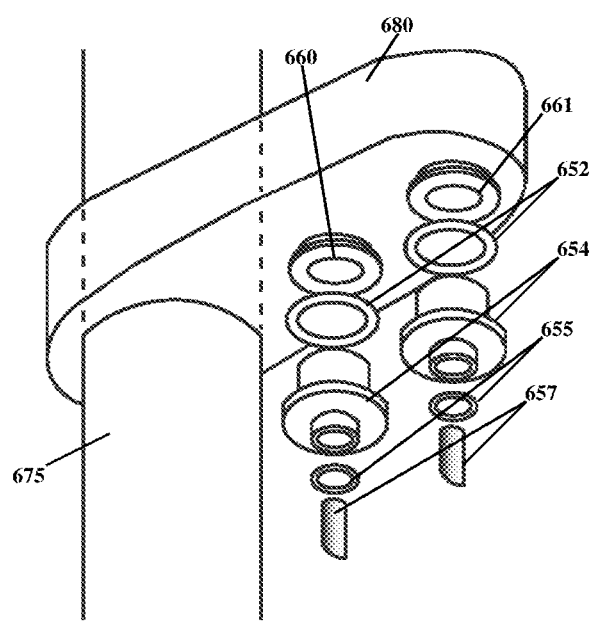
Figure 7D:
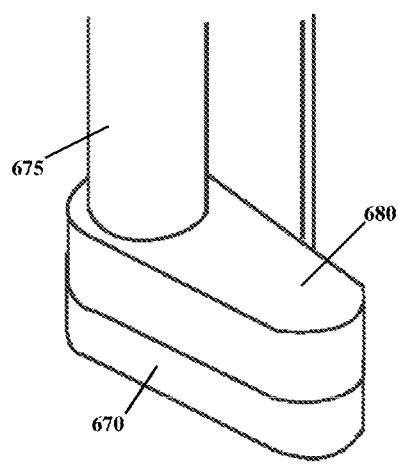
Figure 8A:
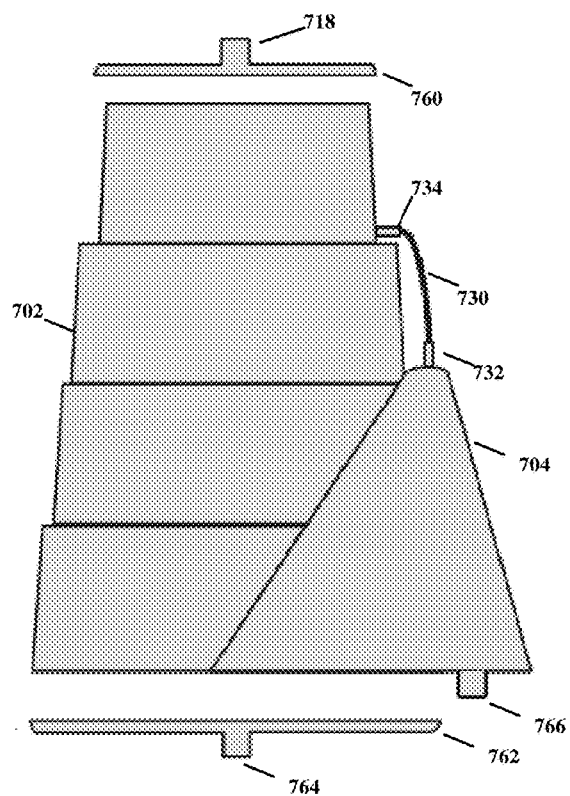
FIGS. 8A through 8C show an alternate embodiment of a sorbent cartridge having first and second flow paths.
Figure 8B:
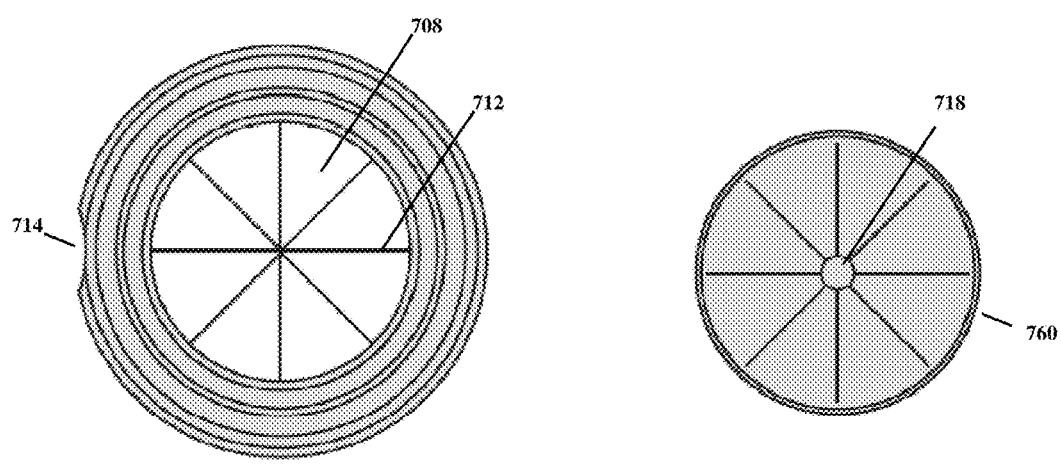
Figure 8C:
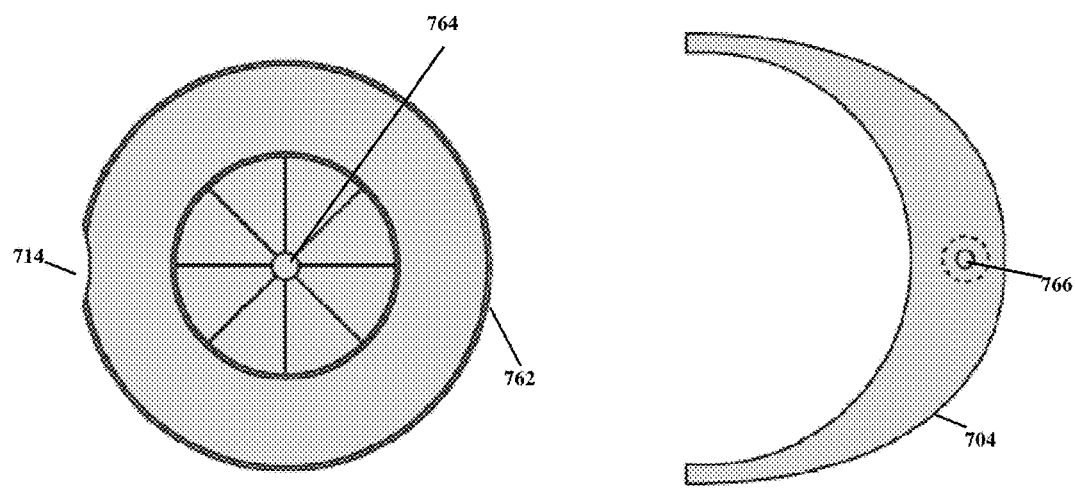

FIG. 7C shows access terminal 660 on the upper arm 680 in more detail. Access terminal 660 has like elements as access terminals 645 and 650 including main terminal body 654, o-rings 652 and 655 and male adapter piece 657 for interfacing with a sorbent cartridge outlet port, such as outlet port 418 shown in FIGS. 3 through 5. The upper arm 680 can also have a rinse port 661 for complementing access terminal 650 in a rinse mode. As shown in FIG. 7D, the upper arm 680 and the lower arm 670 can be brought together to perform a rinse when a sorbent cartridge is not present. The rinse position allows for fluid to be circulated in a connected dialysis circuit including a cleaning fluid that may otherwise damage the sorbent cartridge. In certain embodiments, a cleaning solution contains one or more of citric acid or acetic acid. An additional embodiment for a sorbent cartridge 102 is shown in FIGS. 8A through 8C. FIG. 8A shows two separate housings for housing sorbent materials. Cartridge body 702 can contain one or more than one sorbent material and consists of one flow path for dialysate entering inlet port 764 and exiting outlet port 718. Cartridge body 704 contains at least one sorbent material and a single flow path for dialysate entering inlet port 766 and exiting outlet port 732. The fluid flow exiting outlet port 732 is conveyed to a side port 734 of the housing 702 via conduit 730, such that fluid exiting outlet port 732 comes into contact with one or more sorbent materials housed in the cartridge body 702. The side port 734 is not limited to any particular location on the cartridge body 702.

As shown in FIGS. 8A and 8C, the cartridge body 702 has a circular cross-sectional shape and the cartridge body 704 has a "crescent" cross-sectional shape located adjacent to the housing 702. The cartridge bodies 702 and 704 integrated into a hemodialysis system to function as a sorbent cartridge 102 presents two flow paths for dialysate entering the sorbent cartridge to travel. A first flow path enters the cartridge body 702 through inlet port 764 and comes into contact with the one or more sorbent materials present in cartridge body 702. The second flow path enters the cartridge body 704 through inlet port 766 and contacts at least one sorbent material located therein followed by contact with at least one sorbent material located in cartridge body 702. The division of dialysate flow between input ports 764 and 766 can be performed in the same manner as between inlet ports 464 and 466 described above.

In certain embodiments, the cartridge body 704 contains a mixed bed de-I material and the cartridge body 702 contains a zirconium phosphate material. In certain other embodiments, the cartridge body 702 can contain additional sorbent materials in addition to zirconium phosphate including zirconium oxide, activated carbon and a urease-containing material. The side port 734 can be positioned in a location such that fluid traveling the second flow path entering inlet port 766 contacts one or more sorbent materials within the cartridge body 702 with the proviso that the fluid does not contact a zirconium phosphate material.

Dialysate entering the cartridge body 704 becomes substantially deionized due to contact with the mixed bed de-I material found therein. As such, $Mg^{2+}$, $Ca^{2+}$ and $K^+$ found with the dialysate entering the cartridge body 704 is not absorbed by a zirconium phosphate material allowing for the absorption capacity of any zirconium phosphate material found in cartridge body 702 to be preserved. The fluid generated at outlet 732 can then be contacted with non-zirconium phosphate materials in the cartridge body 702, such as activated carbon, by location of the side port 734 at a location above any zirconium phosphate material located in cartridge body 702.

FIG. 8B shows a top view of the cartridge body 702. The cartridge body 702 has a downstream opening 708 that is optionally crossed by one or more support beams 712 for retaining materials therein. The downstream opening 708 is covered and sealed by a top piece 760, also shown in FIG. 8B, that has output port 718 formed therein.

FIG. 8C shows a bottom piece 762 for sealing an upstream opening of the cartridge body 702 and the bottom of cartridge body 704. As shown, input port 764 is formed in bottom piece 762 and input port 766 is formed in the bottom of cartridge body 704. A notch 714 can be formed in any of the pieces forming the sorbent cartridge to allow for proper alignment.

Quantization of Urea Removal

The blood of patients undergoing a regime of renal replacement therapy typically undergoes blood chemistry determination by laboratory testing on a periodic basis to determine the effectiveness of treatment. Such testing is undertaken by a trained healthcare professional on a separate basis from the renal replacement therapy. Based upon lab results, various treatment metrics can be adjusted. For a patient utilizing the wearable sorbent system described herein without the aid of a healthcare professional, it is desirable to have a facility to determine the accuracy of treatment during therapy.

During treatment, the sorbent cartridge acts as a cation exchanger and releases hydrogen and sodium ions. The release of sodium by the sorbent cartridge has two principal sources:

1) Urea is converted to ammonium ions by the urease layer of the sorbent cartridge. The ammonium ions are exchanged to sodium and hydrogen in the zirconium phosphate layer(s) of the sorbent cartridge. The stoichiometry of the amount of sodium given off in this exchange is dependent on the processing of the zirconium phosphate layer; however, each process provides uniform results. Once the stoichiometry of ammonium/hydrogen/sodium exchange is known, the amount of sodium released from the sorbent cartridge can be used to quantify the amount of ammonium ions absorbed. By means of example, a representative example of the zirconium phosphate material can operate to exchange 1 mEq ammonium ion for 0.15 mEq sodium ion and 0.85 mEq hydrogen ion. In this example, if the cartridge removes 20 grams of urea during a treatment, then the zirconium phosphate material removes 1400 mEq ammonium ions, which would produce about 210 mEq of sodium ions. Those skilled in the art will readily recognize that other zirconium phosphate materials having a different stoichiometry of ammonium/hydrogen/sodium exchange can also be used to calculate the amount of urea converted to ammonium ion and absorbed by the sorbent cartridge; and 2) The dialysis solution contains electrolytes such as calcium ($Ca^{2+}$), magnesium ($Mg^{2+}$) and potassium ($K^+$). These electrolytes remain in a stable range and close to constant in the dialysate during treatment. These electrolytes are totally removed from the spent dialysate by the sorbent cartridge. To ensure that there is a stable and correct concentration of electrolytes in the refreshed dialysate prior to reaching the dialyzer, zirconium phosphate exchanges these electrolytes with sodium ions. Then, the electrolytes are re-infused via an infusate pump to the correct concentrations. The amount of sodium produced from the zirconium phosphate layer due to this exchange is dependent on the dialysis solution flow rate, the time of treatment and the concentration values of these cations in the dialysis solution. For example, if the $Ca^{2+}$ were 3 mEq, the $Mg^{2+}$ 1 mEq, and the $K^+$ 1 mEq, the sorbent cartridge would produce approximately 240 mEq of sodium at a 20 ml/min flow rate and a total volume of 48 liters through the cartridge.

Due to the near constant amounts of ($Ca^{2+}$), magnesium ($Mg^{2+}$) and potassium ($K^+$) ions being exchanged by the sorbent cartridge, the conductivity difference between dialysate containing urea entering the sorbent cartridge compared with the refreshed dialysate exiting the sorbent cartridge can be used to quantify the amount of urea converted to ammonium ions and absorbed by the sorbent cartridge. If the temperature and composition of an electrolyte solution are constant, the resulting conductivity of the solution will remain stable. At the ranges of typical dialysis solutions, any change in sodium concentration will result in a linear increase or decrease in dialysate conductivity. Table 1 shows the concentration and conductivity of a typical dialysis solution at 25° C. Even though sodium is not the only contributor to conductivity in dialysis solution, NaCl and $NaHCO_3$ make up approximately 94% of the conductivity of a typical dialysate solution. There is also typically a small amount of acetic or citric acid and dextrose in the solution.

TABLE 1

Composition of a typical dialysate solution and conductivity contributed by individual species

| Substance | mmol/L | mS/cm |
|---|---|---|
| NaCl | 103 | 10.68 |
| $NaHCO_3$ | 34.0 | 2.47 |
| KCl | 2.00 | 0.26 |
| CaCl | 1.75 | 0.35 |
| MgCl | 0.50 | 0.09 |
| $NaCH_3COO$ | 3.00 | 0.21 |
| Total Conductivity 25° C. | | 14.05 |

Sodium concentration increases in the dialysate due to the exchange of ammonium to sodium, which can be used to verify if the urea was removed during the course of treatment. As shown in FIG. 2, conductivity meters 101, 104 and 160 can be incorporated into the system to measure the conductivity of dialysate traveling to the inlet 197 and exiting the outlet 195 of the sorbent cartridge 102. In certain embodiments, a conductivity meter can be present within the sorbent cartridge at the outlet of the zirconium phosphate layer 320. A conductivity at the inlet of the sorbent cartridge 102 is measure at a location between the dialysate outlet 196 of the dialyzer 130 and the sorbent cartridge 102. A conductivity at the outlet of the sorbent cartridge 102 is measured at a location between the sorbent cartridge 102 and the dialysate inlet 194 of the dialyzer 130. A microprocessor or controller 801 can monitor the conductivity measured by the conductivity meters to analyze the changes in conductivity brought about by the following:

1) Conversion of urease to ammonium carbonate and subsequent exchange of ammonium carbonate to sodium, and
2) Any net change in conductivity due to the exchange of $Ca^{2+}$, $Mg^{2+}$, and $K^+$ into sodium, which can be treated as a constant value. The change due to removal of $Ca^{2+}$, $Mg^{2+}$, and $K^+$ is known and the increase due to sodium is known. In the example dialysis solution of Table 1, the $Ca^{2+}$, $Mg^{2+}$, and $K^+$ contribute 0.7 mS/cm of conductivity.

The change in conductivity due to the loss of $Ca^{2+}$, $Mg^{2+}$, and $K^+$ and the increase of sodium ions due to this exchange will be relatively constant during the treatment. Further, the fraction of the dialysate flow traveling through the second flow path 260, shown in FIG. 1, is known and monitored by the controller 801. As such, the controller 801 can readily calculate the change in conductivity that is the result of urea absorption by the sorbent cartridge 102. From this information, a controller can then calculate the amount of conductivity increase due to the urea removal via the following sources:

Inlet Conductivity−Conductivity Contribution of $Ca^{2+}$, $Mg^{2+}$, and $K^+$=Starting Conductivity Outlet Conductivity−Increase in Conductivity due to exchange of $Ca^{2+}$, $Mg^{2+}$, and $K^+$ to $Na^+$+the decrease in conductivity due to the de-I resin=Corrected Outlet Conductivity Corrected Outlet Conductivity−Starting Conductivity=Conductivity Increase due to Conversion of $NH_4^+$ to $Na^+$ The following example quantization is based upon 48 liters of regenerated dialysis solution used during the course of treatment having typical concentrations of $Ca^{2+}$, $Mg^{2+}$, and $K^+$, where 100% of the dialysate flow is conveyed through the first flow path 250 of FIG. 1:

Inlet Conductivity=14.04 mS/cm Outlet Conductivity=14.32 mS/cm 1. 14.05 mS/cm−0.7 mS/cm=13.35 mS/cm Starting Conductivity
2. 14.32 mS/cm−0.5 mS/cm=13.8 mS/cm Corrected Outlet Conductivity
3. 13.8 mS/cm−13.35 mS/cm=0.45 mS/cm Conductivity Increase due to Conversion of $NH_4^+$ to $Na^+$
4. 0.45 mS/cm/0.1037 mS·L/mEq·cm=4.34 mEq/L $Na^+$ due to Urea Removal
5. 0.4 g urea per liter In hemodialysis, urea removal depends on the diffusive gradient across the dialyzer membrane. This gradient will be much higher at the beginning of treatment than at the end of treatment when typically 50 to 60 percent of the patient's urea has been removed. In certain embodiments, the conductivity values can be averaged so the curve of urea removal is understood and a continuous calculation need not be made. For example, conductivity can be sampled four or five times per treatment session for the purposes of quantifying urea removal. Early during a treatment session, a quantization of urea removal can be performed to verify that urea is being removed and that the Na$^+$ increase is relatively high. Later, quantization measurements can be performed to calculate a curve for urea removal and to predict total expected urea removal based on this curve. As such, the amount of urea removed during treatment can be either accurately measured or estimated with a high degree of certainty.

Detection of Significant Clearance Problems

The urea removal monitoring facility described above can be used to indicate the proper operation of the system and to alert the patient to significant problems that would interrupt the waste removal process. This problem could be communicated automatically via WiFi, the internet, or other communication means to the doctor or healthcare professional. For instance a patient with impaired blood access flow would have little urea removed. In instances were low urea removed is monitored toward the beginning of treatment, an alarm can be communicated indicating a potential malfunction.

Access to the patient's vasculature can fail due to a buildup of plaque in the access stent. This plaque creates a stenosis at the distal end of the anastomosis where the stent or graft is sutured to the vascular system of the patient. When this occurs, the blood tends to recirculate within the access area and there is a lack of adequate flow of fresh blood into the extracorporeal circuit, which can result in the same blood being repeatedly dialyzed. Since little blood entering the dialyzer is from the systemic circulation, there is less urea in the blood and hence less sodium is produced from the cartridge due to urea/ammonium to sodium exchange. The lack of an adequate increase in conductivity can be detected by the system and an alert can be sent indicating a potential malfunction or problem accessing the patient's vascular system. This alert can indicate a lowered waste clearance, but the alert does not necessarily specify if the cause of the lowered waste clearance is due to a vascular access problem or due to a problem in dialysis flow, etc. A skilled medical professional can analyze the event to determine the cause of the alert in some embodiments.

Detection of Zirconium Exhaustion

After an extended period of use, the ability of the zirconium phosphate to absorb urea can be exhausted. Exhaustion of zirconium phosphate leads to ammonium release into the dialysate, which can lead to ammonium intoxication in the patient. As discussed above, the exchange of urea/ammonium to sodium affects the output conductivity of the sorbent cartridge. Monitoring the inlet and outlet conductivities of the cartridge thus provides a method to detect ammonium breakthrough in the sorbent cartridge. An equilibration of the sorbent cartridge inlet conductivity with the output conductivity over a short time period indicates that the zirconium phosphate layer within the sorbent cartridge is exhausted. In certain embodiments, the conductivities pre- and post-sorbent cartridge are monitored. If an increase in sodium concentration is not detected by the controller, then the system will send an alert and prevent the dialysate from reaching the dialyzer, thus protecting the patient from ammonia intoxication.

Detection of Patient Hydration Status

The portable dialysis described herein can be used to perform ultrafiltration on a patient. During ultrafiltration, fluid is drawn out from the serum of the blood in the extracorporeal circuit through the dialysis membrane 135 by means of the control pump 190. Fluid removed by the control pump 190 is removed to the control reservoir 192. Ultrafiltration can be performed alone or in conjunction with convective clearance, as described above.

Patients having kidney failure may have an undesirable accumulation of fluid in body tissues that is called edema. As fluid (e.g. water) is removed from the patient's plasma, the volume of the patient's plasma is replaced by infusion of fluid from the patient's tissues. That is, the portable dialysis system does not directly access fluids stored in the patient generally but only directly accesses the patient's vascular system. Humans typically only have 5 to 6 L of plasma volume at any one time, where a significant time lapse can be required for plasma volume to be replaced by transfer to fluid from surrounding tissues.

During ultrafiltration, fluid can be removed too rapidly resulting in the patient becoming hypovolemic, which can cause several serious effects including hypotension, cramping, nausea and vomiting. To avoid instances of hemoconcentration due to excessive fluid removal, the rate of ultrafiltration is limited to a percentage of the blood flow through the extracorporeal circuit 140. In certain embodiments, the rate of ultrafiltration is limited to be no greater than about 30% of the plasma flow through the extracorporeal circuit 140. Plasma flow (Qp) is defined as Qp=Blood flow rate×(1−hematocrit), where blood flow rate is in units of volume divided by time (e.g. mL/min) and hematocrit is the unitless fraction of blood volume occupied by red blood cells. For example, if the blood flow rate is 60 mL/min and the hematocrit is 40%, then the maximum rate of ultrafiltration is set to be equal to about 10.8 mL/min or less.

The portable dialysis system can have a hematocrit detector to determine the hematocrit of blood containing within the extracorporeal circuit 140 of FIG. 2. In certain embodiments, the hematocrit detector is a light source and a photodetector, wherein light emanating from the light source is passed through the blood in the extracorporeal circuit 140 and detected by the photodetector. The absorption of one or more wavelengths of light can indicate the level of hematocrit in blood entering the dialyzer 130 in the arterial line 610. In certain embodiments, the hematocrit detector gives an indication if the hematocrit trend is unsafe rather than giving a precise numerical quantification. In certain additional embodiments, the hematocrit detector can also determine if blood is present in the extracorporeal circuit 140, which can be useful during the processes of priming the system or returning blood to the patient as described above. A simple optical detector with a light source and a photodetector can also be used to detect whether there is blood in the system.

In most renal diseases, the kidneys fail to produce erythropoietin, a hormone that stimulates red blood cell production. Most ESRD patients take an erythropoietin stimulation drug to help produce red blood cells. These drugs are dosed to maintain a pre-treatment serum hematocrit of 32%. During the course of the dialysis treatment, the hematocrit can change due to the removal of fluid from the blood. Hematocrit level changes over the course of the treatment are an indication of relative blood volume changes over treatment. Fluid removal by ultrafiltration removes fluid from the blood plasma; however, red blood cells are left in the circulatory system. Depending on the rate of vascular fluid refilling from the tissues, the hematocrit will increase or decrease. A flat hematocrit indicates that the patient is most likely fluid overloaded even at the end of therapy. A steep increase in the slope of the hematocrit during fluid removal may portend a hypovolemic event prior to initiating a hypotensive episode. A gradual increase in hematocrit during the course of treatment is most likely indicative of a well-dialyzed patient.

Figure 9:
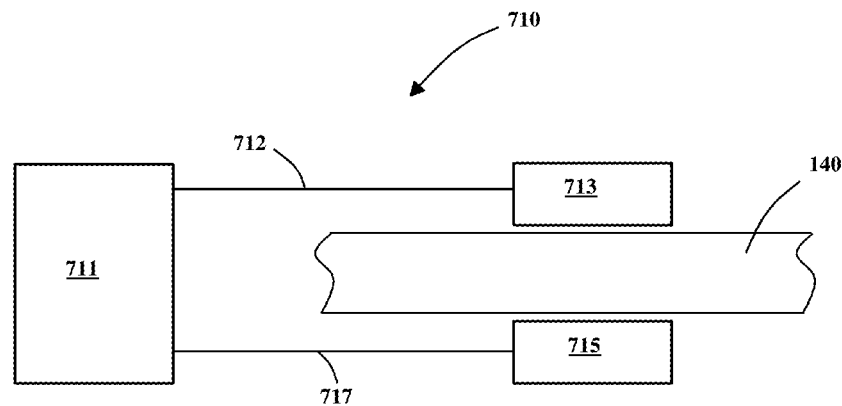
FIG. 9 shows a schematic for a hematocrit detector.

Hematocrit level is proportional to hemoglobin concentration. Therefore, any suitable sensor can be used to measure hemoglobin concentration, such as sensors used in pulse oximeters which measure adsorption of red and infrared light to determine concentration of oxygenated hemoglobin and deoxyhemoglobin, respectfully. The hematocrit/hemoglobin sensors, which may include the associated light source(s), can be placed in any suitable location. Placement of the hematocrit/hemoglobin sensor along the arterial line 610 of the extracorporeal circuit 140 will indicate the status of blood volume within the circulation of the patient. Placement of the hematocrit/hemoglobin sensor along the venous line 620 of the extracorporeal circuit 140 will indicate the extent of hemoconcentration occurring within the dialyzer 130. Measurement of hematocrit within the arterial line 610 can be used to calculate Qp as described above. Other optical based technologies that can determine the relative blood volume changes during the course of treatment can also be used to determine hydration status of the patient and whether the appropriate amount of fluid has been removed FIG. 9 shows a schematic for a hematocrit/hemoglobin/relative blood volume sensor. A light source 713 of appropriate wavelength (red or infrared) is positioned on one side of the tubing of extracorporeal circuit 140 such that the light passing through tubing hits detector 715. More light is absorbed (and less hits the detector 715) if a higher concentration of hemoglobin is present in the extracorporeal circuit 140. A lead 712 carries power and other electrical signals, if appropriate, to the light source 713 from the sensor device body 711, which may contain the power source and other control or detecting electronics. Lead 717 carries electrical signals from detector 715 to the components housed in sensor device body 711. Suitable hematocrit sensors are known, such as a CRIT-LINE monitor from HEMAMETRICS (see, HEMAMETRICS, CRIT-LINE hematocrit accuracy, Vol. 1, Techn Note No. 11 (Rev. D) Feb. 24, 2003).

In other embodiments, hemoconcentration and blood hydration can be detected and monitored by a relative blood volume monitor. The relative blood volume monitor can detect a change in the concentration of measured solutes, solid materials or group of solutes and solid materials in the blood that are too large to cross the dialysis 135 or hemofiltration 200, which indicates a change in blood volume. The volume of blood typically is not measured by the relative blood volume monitor. The relative blood volume monitor measures the change in water content of the blood over the course of treatment indirectly by measuring a solute or solid material and does not require an absolute quantization of any particular solute in the blood. The relative blood volume monitor determines the relative blood volume hydration status (RBVHS) of the subject by measuring the level of one or more blood solutes at a time close to the beginning of treatment, which can be assigned a value $C_0$. The level of the one or more blood solutes does not require an absolute quantification, rather the level of the one or more blood solutes can be reported as the magnitude of a signal generated by the relative blood volume monitor. The level of the one or more solutes is measured periodically at a second later time, which can be assigned a value $C_t$. The relative blood volume hydration status can then be determined by the formula $RBVHS=C_0/C_t$.

In certain embodiments, the relative blood volume monitor is a hematocrit sensor and the one or more solutes measured by the relative blood volume monitor are oxygenated or deoxygenated hemoglobin. In certain other embodiments, the relative blood volume monitor is a device that measures the velocity of ultrasonic sound waves in the blood. Ultrasonic sound waves are defined as sound waves having a frequency above 20,000 Hz. The velocity of ultrasonic sound waves in blood is an indication of the total protein concentration in the blood.

The relative blood volume hydration status can be used in the same manner as hematocrit, described above, to determine the effectiveness of ultrafiltration. It is important to note that when using relative blood volume the trend slope is inverse to using a hematocrit sensor. As hematocrit increases, relative blood volume decreases, i.e. as hematocrit increases, relative blood volume decreases. A flat relative blood volume hydration status indicates that the patient is most likely fluid overloaded even at the end of therapy. A steep decrease in the slope of the relative blood volume hydration status during fluid removal can portend a hypovolemic event prior to initiating a hypotensive episode. A gradual decrease in relative blood volume hydration status during the course of treatment is most likely a well-dialyzed patient. In certain further embodiments, the relative blood volume hydration status determined by the relative blood volume monitor can be correlated to a fluid volume of the blood.

In the event that an unsafe level of hydration status is indicated by hematocrit level or by relative hydration status, a controller 801 associated with the system can stop the fluid removal and alert the patient. Controller 801 can be programmed to remove fluid via a gradual slope down in relative blood volume or up when monitoring hematocrit or another indicator of relative blood volume. Additionally, the controlled compliant nature of the dialysis circuit can be used to administer a bolus transfer of fluid to the patient. As described above, operation of the control pump 190 in the influx direction will cause a transfer of fluid volume from the control reservoir 191 to the extracorporeal circuit 140. The system can be preprogrammed to transfer a certain bolus volume to the patient upon detection of an unsafe trend in hematocrit or relative blood volume hydration status.

In certain embodiments, the control reservoir 191 is empty at the beginning of a treatment session wherein volume enters the control reservoir during treatment including ultrafiltration. As such, a bolus infusion in response to trend in hematocrit or relative blood volume hydration status is a return of fluid volume removed from the patient during treatment back to the patient. Any volume returned to the patient from the control reservoir 191 is cleaned by the sorbent cartridge 102 prior to introduction to the extracorporeal circuit 140. However, in other embodiments the control reservoir 191 can contain a volume of fluid at the beginning of treatment that can be used for a net infusion of fluid into the patient during the course of treatment.

Figure 10:
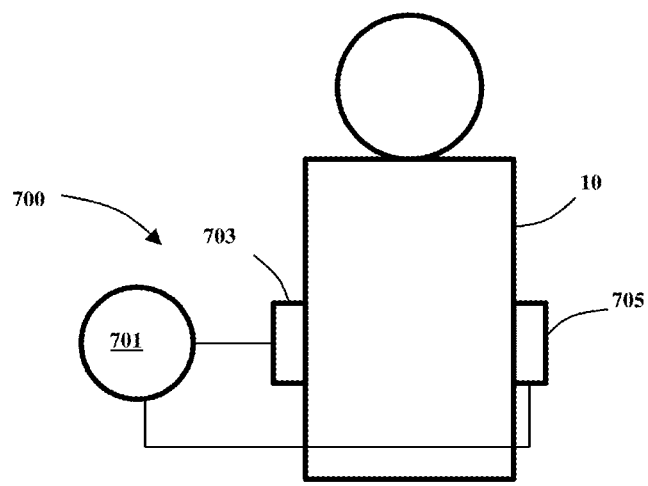
FIG. 10 shows a schematic for an impedance detector.

Hypovolemia can further be guarded against by simultaneously monitoring body fluid level of the patient undergoing hemodialysis treatment. The amount of fluid stored in body tissues outside the blood is proportional to the impedance that can be measured from the patient's body. As depicted in FIG. 10, impedance can be monitored between two electrodes 703 and 705 that are attached to the torso 10 of a human patient. The electrodes 703 and 705 are operably coupled to control and processing electronics 701 via leads. The electronics 701 are configured to generate a voltage differential between the electrodes 703 and 705, and current can be measured and impedance calculated. The measurement can be done in either DC or AC mode. Impedance or phase angle can be correlated to tissue fluid volume. Suitable external impedance monitors 700 and components that can be used in accordance with the teachings described herein are known. In certain other embodiments, electrodes 703 and 705 can be implanted within the patient.

One example of a well studied system that can be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., Siegenthalar, et al. Journal of Clinical Monitoring and Computing (2010): 24:449-451, and Wang, Am. J. Cardiology, 99(Suppl):3G-1-G, May 21, 2007. Alternatively or in addition, tissue impedance can be monitored for a suitable period of time to establish as suitable baseline, and patient markers can be used to instruct whether the patient is fluid overloaded or under-loaded. The data acquired by impedance sensor and input data regarding fluid status of the patient at the time the sensor data is acquired may be used to establish suitable ranges for impedance values.

One or more controllers 801 associated with the hemodialysis system can monitor the hematocrit/relative blood volume hydration status and impedance/body fluid level of the patient undergoing hemodialysis treatment. A typical hematocrit level for a dialysis patient is about 32%. Prior to a treatment session, the fluid volume of blood of a kidney disease patient can be elevated, thus hematocrit levels can be lower than desired. The one or more controllers 801 monitoring hematocrit levels can adjust the rate of fluid removal or end ultrafiltration treatment when hematocrit level reaches the desired, predetermined range.

Fluid within a person's body is capable of moving from the body tissue to the blood and vice versa. As such, proper fluid levels in a patient can be described in terms of a ratio of tissue fluid to blood volume, as measured by hematocrit level. Hematocrit level of body fluid level can be monitored independently as described above. In general, blood is about 7% of body weight and total tissue fluid is about 60% of the body weight (including blood, extracellular and intracellular fluid). As such, a typical tissue fluid to blood fluid volume ratio of a healthy individual is in the range from about 6:1 to about 9:1. A measured ratio above this range indicates that blood is being withdrawn too quickly to allow for adequate equilibration of fluid between the blood and tissues of the patient. Fluid removal can be modified, stopped, or a fluid bolus administered as appropriate and preprogrammed into the one or more controllers 801 of the hemodialysis system.

Detection of Needle or Catheter Disconnection

It is well established in the art that pressure is not always a reliable means to detect separations of the venous blood return from the access of the patient. If this event occurs there is the risk of a life threatening blood loss and possible exsanguination. A conductive mat or holder can be used to detect blood leaks to the controller. The controller can then take the appropriate means to protect the patient by stopping the blood pump and alerting the patient. Other means to detect needle or catheter disconnections can be incorporated into the system such as monitoring of the impedance through the two needles or using pressure pulses.

System Control

As described above, the systems described herein have several dynamic components including pumps and valves as well as detectors that determine the state of the system. As applied throughout this disclosure, operation of the system under the control of a controller can refer to a single controller or multiple controllers having separate or overlapping function. A controller refers to a device having a programmable microprocessor and associated memory.

Figure 11:
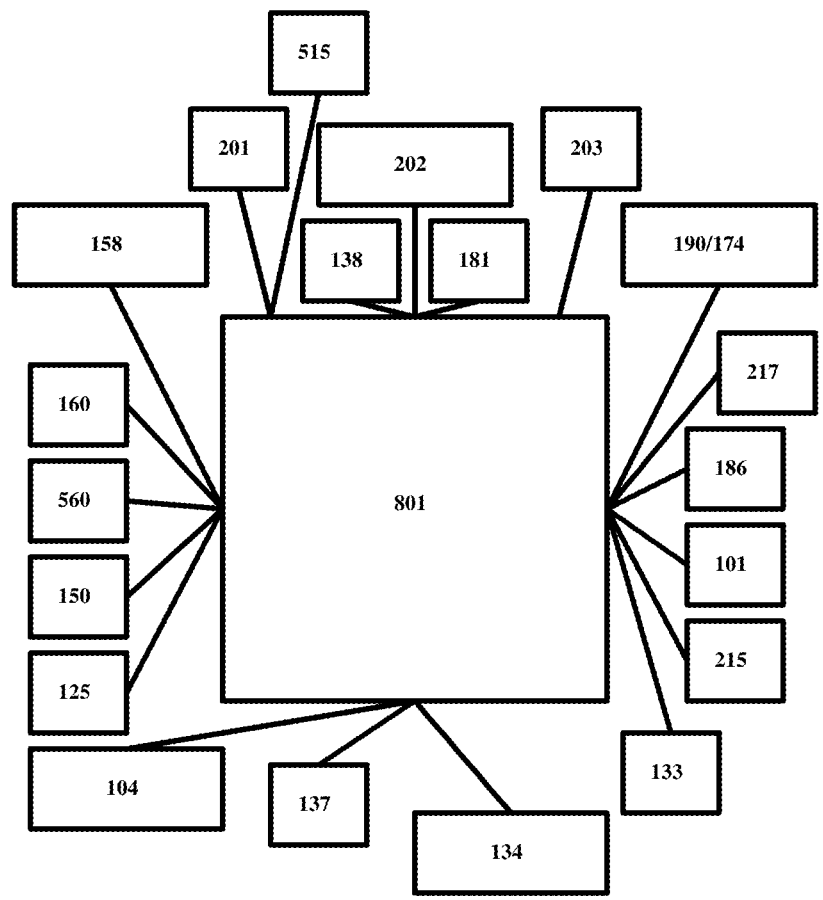
FIG. 11 shows a schematic for a controller in communication with various system components.

FIG. 11 shows one or more controllers 801 capable of sending and receiving data or instructions from several system components. The one or more controllers 801 can be more than one microprocessor unit. Specifically, the one or more controllers 801 are capable of controlling the pump rate and pumping direction of the blood pump 125, the dialysate pump 138, second reservoir pump 174, the infusate pump 181, and the control pump 190 along with the operating of valve 150, valve 158, valve 215, valve 217, and valve 515. The operation of anticoagulant pump 186 is further under control of the one or more controllers 801. In two controller systems, one controller can be used to control the process and the other controller may be used to monitor the system and protect if the control is not correct. Alternatively in one controller systems, the processes that control or protect may be separate processes within the same controller.

The one or more controllers 801 also receives data from the various meters and detectors incorporated in the system including pressure meters 133, 134, and 137, air-fluid detectors 201, 202, and 203, conductivity detectors 101, 104 and 160 and blood leak detector 560. The one or more controllers 801 are capable of stopping or modifying operation of the system to protect the patient from an unsafe pressure reading indicating a malfunction or the presences of air in the extracorporeal circuit 140, an unsafe conductivity level or detection of a blood leak in the dialyzer 130, as detected by blood leak detector 560. The one or more controllers are capable of stopping any of the pumps of the systems or operating valve 150 to bypass the dialyzer 130. Further, the one or more controllers 801 can modify or stop the operation of the system based upon the conductivity readings from the conductivity meters 101, 104 and 160 as well as calculating an amount of urea absorption by the sorbent cartridge 102 and/or sodium entering or leaving the system through control pump 190. In two controller systems one controller may be used to control the process and the other controller may be used to monitor and protect if the control is not correct.

In certain embodiments, the one or more controllers 801 are located remote from the dialysis and extracorporeal circuits. One of the controllers 801 can be a device that can send and receive data and instructions through a wired or wireless connection with the portable dialysis system. Certain controller functions, for example, can be performed by an application that runs on a multipurpose computing device such as a cell phone, tablet, PC or PDA. In certain embodiments, a controller 801 that is remote to the portable dialysis system is capable of operating through a wired connection to the portable dialysis system to enable operation in hospital environments or airplanes where the use of wireless technology is restricted.

By locating one or more of the controllers 801 remote from the portable dialysis system, the majority of processing power does not have be carried by the patient thereby lowering the weight of the device. Devices and methods for controlling a device through wireless technology are known in the art. The wireless signals can employ signal confirmation, digital encoding algorithms, checksums and other verifications to minimize the effects of interference and to allow similar systems to operate in the same area. The system can have a safety feature to stop the device if the wireless control signal is interrupted or compromised.

It will be apparent to one skilled in the art that various combinations and/or modifications and variations can be made to the portable dialysis system depending upon the specific needs for operation. Moreover, features illustrated or described as being part of one embodiment may be used on another embodiment to yield a still further embodiment.

We claim:

1. A sorbent cartridge, comprising:
   at least one cartridge body having a first inlet port and a second inlet port,
   a common conduit;
   one or more valves to direct dialysate to travel from the common conduit to either the first inlet port that defines a first flow path or the second inlet port that defines a second flow path through the sorbent cartridge to an outlet port; and
   the first flow path flowing through at least a urease containing material and a zirconium phosphate material in the cartridge that is not in fluid communication with the second flow path, the second flow path flowing through at least a mixed anion and cation de-ionization resin in the sorbent cartridge not in fluid communication with the first flow path; wherein the sorbent cartridge is capable of removing at least one impurity or waste species from a fluid.

2. The sorbent cartridge of claim 1, wherein the first flow path can further pass a fluid through any one of a zirconium oxide material and an activated carbon material and combinations thereof, and the second flow path can further pass a fluid through an activated carbon material.

3. The sorbent cartridge of claim 1, wherein the sorbent cartridge further comprises a second cartridge body, wherein the first inlet port allows a fluid to enter one cartridge body and the second inlet port allows a fluid to enter the second cartridge body.

4. The sorbent cartridge of claim 3, wherein the second cartridge body has an outlet port attached to a conduit for passing fluid to a side port of another cartridge body.

5. The sorbent cartridge of claim 1, wherein the sorbent cartridge comprises:
   one cartridge body having a top portion and top portion sidewall and a bottom portion and bottom portion sidewall, the bottom portion having a larger mean diameter than the top portion, wherein a downstream opening and an upstream opening of the cartridge body are substantially parallel.

6. The sorbent cartridge of claim 5, further comprising one or more molded housings present within the cartridge body, wherein a first interior space is formed between a downstream opening of one of the molded housings and the downstream opening of the cartridge body with the proviso that the first interior space is not interior to the one or more molded housings.

7. The sorbent cartridge of claim 6, wherein the one or more molded housings include at least one selected from a first molded housing having a second interior space formed from one or more sidewalls and the one or more sidewalls forming a downstream opening and an upstream opening to the first molded housing; and a second molded housing having a third interior space formed from one or more sidewalls and the one or more sidewalls forming a downstream opening and an upstream opening to the second molded housing.

8. The sorbent cartridge of claim 7, wherein the first molded housing has a plurality of standoffs projecting from the first molded housing in a direction substantially perpendicular to the downstream opening of the cartridge body.

9. The sorbent cartridge of claim 7, wherein a first flow channel space is formed between the one or more sidewalls of the first molded housing and the sidewall of the cartridge body.

10. The sorbent cartridge of claim 6, wherein the second molded housing has an annular peripheral portion having a plurality of openings formed therein.

11. The sorbent cartridge of claim 6, where the downstream opening and upstream opening of the second molded housing are parallel to the downstream opening and upstream opening of the cartridge body, and a fourth interior space is formed between the one or more sidewalls of the second molded housing and the one or more sidewalls of the cartridge body.

12. The sorbent cartridge of claim 6, wherein the one or more molded housings include a first molded housing having a second interior space formed from one or more sidewalls and the one or more sidewalls forming a downstream opening and an upstream opening to the first molded housing, and
   wherein the one or more molded housings include a second molded housing having a third interior space formed from one or more sidewalls and the one or more sidewalls forming a downstream opening and an upstream opening to the second molded housing and a fourth interior space is formed between the one or more sidewalls of the second molded housing and the one or more sidewalls of the cartridge body.

13. The sorbent cartridge of claim 12, wherein a first flow channel space is formed between the one or more sidewalls of the first molded housing and the sidewall of the cartridge body, wherein the fourth interior space is in fluid communication with the first flow channel space.

14. The sorbent cartridge of claim 13, wherein the first molded housing has a plurality of standoffs projecting from the first molded housing in a direction substantially perpendicular to the downstream opening of the cartridge body and a second flow channel space is formed between a base of the plurality of standoffs and a sorbent material in the first interior space.

15. The sorbent cartridge of claim 12, wherein the second molded housing has an annular peripheral portion having a plurality of openings formed therein and the annular peripheral portion contacts the one or more sidewalls of the cartridge body.

16. The sorbent cartridge of claim 12, wherein a fluid introduced to the first inlet port passes through the third interior space but does not pass through the fourth interior space.

17. The sorbent cartridge of claim 12, wherein a fluid introduced to the second inlet port passes through the fourth interior space but does not pass through the third interior space and/or the second interior space and/or the first interior space.

18. The sorbent cartridge of claim 12, further comprising a bottom piece attached to the one cartridge body, wherein the first inlet port and the second inlet port are formed in the bottom piece.

19. The sorbent cartridge of claim 12, wherein the first flow path comprises the first interior space, the second interior space and the third interior space.

20. The sorbent cartridge of claim 12, wherein the second flow path comprises the fourth interior space, the first interior space and the first flow channel space.

21. The sorbent cartridge of claim 5, wherein the one cartridge body can have any one of a tapered, cylindrical, conical, or mesa shape.

22. The sorbent cartridge of claim 1, wherein the sorbent cartridge is docked in a cartridge holder, the cartridge holder comprising:

a central shaft;

a first arm attached to the central shaft having first and second access terminals;

a second arm attached to the central shaft having an access terminal, the second arm movable between at least a first position and a second position, wherein the first access terminal of the first arm is engaged with the first inlet port, the second inlet access terminal of the first arm is engaged with the second inlet port and the access port of the second arm is engaged with the outlet port.

23. A method comprising:

measuring the conductivity of a fluid prior to entering a sorbent cartridge;

wherein the sorbent cartridge comprises at least one cartridge body; a common conduit; one or more valves to direct dialysate to travel from the common conduit to either a first inlet port that defines a first flow path or a second inlet port that defines a second flow path through the sorbent cartridge to an outlet port;

dividing the fluid between the first inlet port and the second inlet port of the sorbent cartridge based upon the conductivity of the fluid;

removing one or more waste species from the fluid and adjusting the sodium ion concentration of the fluid; and recovering the fluid from the outlet port of the sorbent cartridge wherein the first flow path connected to the first inlet port includes a urease material and a zirconium phosphate material that is not in fluid communication with the second flow path; and wherein the second flow path is connected to the second inlet port including a mixed anion and cation de-ionization resin in the sorbent cartridge not in fluid communication with the first flow path.

24. A system for performing kidney replacement treatment, comprising:

a hemodialysis system having a controlled compliance dialysis circuit, a dialyzer with a high permeability dialysis membrane, a blood inlet end for receiving blood, a blood outlet end for allowing blood out of the dialyzer, a dialysate inlet end for receiving dialysate and a dialysate outlet end for allowing dialysate out of the dialyzer, wherein the blood and the dialysate contact different sides of the dialysis membrane;

an extracorporeal circuit having a conduit for receiving blood from a subject and a conduit for returning blood to the subject and a blood pump for conveying blood from the subject, to the dialyzer and back to the subject; and a dialysis circuit having a sorbent cartridge for removing impurities and waste species from the dialysate, one or more conduits for conveying dialysate between the sorbent cartridge and the dialyzer, and a dialysate pump for conveying dialysate from the sorbent cartridge, to the dialyzer and back to the sorbent cartridge, the sorbent cartridge having a dialysate inlet end and a dialysate outlet end;

wherein the sorbent cartridge comprises:

at least one cartridge body having a first inlet port and a second inlet port; a common conduit; one or more valves to direct dialysate to travel from the common conduit to either a first inlet port that defines a first flow path or a second inlet port that defines a second flow path through the sorbent cartridge to an outlet port; and the first flow path flowing through at least a urease containing material and a zirconium phosphate material in the cartridge body that is not in fluid communication with the second flow path, the second flow path flowing through at least a mixed anion and cation de-ionization resin in the sorbent cartridge not in fluid communication with the first flow path; wherein the sorbent cartridge is capable of removing at least one impurity or waste species from a fluid.

* * * * *